United States Patent
Wang

(10) Patent No.: US 10,180,434 B2
(45) Date of Patent: Jan. 15, 2019

(54) ANTIBODY ARRAY USED FOR THE ANALYSIS OF THE THREE-DIMENSIONAL STRUCTURE OF PROTEIN THERAPEUTICS AND ITS PRODUCTION

(71) Applicant: Array Bridge Inc., St. Louis, MO (US)

(72) Inventor: Xing Wang, Wildwood, MO (US)

(73) Assignee: Array Bridge Inc., St. Louis, MO (US)

( * ) Notice: Subject to any disclaimer, the term of this patent is extended or adjusted under 35 U.S.C. 154(b) by 848 days.

(21) Appl. No.: 14/384,407

(22) PCT Filed: Mar. 12, 2013

(86) PCT No.: PCT/US2013/030456
§ 371 (c)(1),
(2) Date: Sep. 11, 2014

(87) PCT Pub. No.: WO2013/138310
PCT Pub. Date: Sep. 19, 2013

(65) Prior Publication Data
US 2015/0119266 A1   Apr. 30, 2015

Related U.S. Application Data

(60) Provisional application No. 61/610,147, filed on Mar. 13, 2012.

(51) Int. Cl.
| | | |
|---|---|---|
| G01N 33/543 | (2006.01) | |
| G01N 33/68 | (2006.01) | |
| G01N 33/53 | (2006.01) | |
| C07K 16/00 | (2006.01) | |

(52) U.S. Cl.
CPC ......... *G01N 33/6845* (2013.01); *C07K 16/00* (2013.01); *G01N 33/53* (2013.01)

(58) Field of Classification Search
None
See application file for complete search history.

(56) References Cited

U.S. PATENT DOCUMENTS

| | | | | |
|---|---|---|---|---|
| 6,604,052 B1 * | 8/2003 | Jensen | ............... | G06K 9/00134 435/6.11 |
| 2006/0205089 A1 | 9/2006 | Dratz | | |
| 2009/0017553 A1 * | 1/2009 | Hoying | .............. | G01N 21/6428 436/172 |
| 2011/0045572 A1 | 2/2011 | Roggen | | |

FOREIGN PATENT DOCUMENTS

EP   2315143   4/2011

OTHER PUBLICATIONS

Deretic et al., Topographic Analysis of Antigenic Determinants Recognized by Monoclonal Antibodies to the Photoreceptor Guanyl Nucleotide-binding Protein, Transducin, vol. 262, No. 22, Issue of Aug. 5, pp. 10839-10847. (Year: 1987).*
Development of antibody arrays for monoclonal antibody Higher Order Structure analysis, Xing Wang et al. 2013, Antibody Array Paper vol. 4 No. 103, pp. 1-8.
Case Studies of Biosimilar Monoclonal Antibodies, Xing Wang et al. 2014, Biosimilar HOS analysis, BioProcess International vol. 12 No. 6, pp. 2-7.
Physicochemical characterization of Remsima, Soon Kwan Jung, et al. 2014, Celltrion Remsima Report, vol. 6 No. 5 pp. 1163-1177.
New Method for "Fingerprinting" Biosimilars, Comparability Testing Platform for Biologics at Molecular Level Now Available, Michael Davies et al., 2012, Genetic Engineering & Biotechnology News, AssayTutorial, pp. 32-33.
International Application No. PCT/US2013/030456; International Preliminary Report on Patentability, dated Sep. 16, 2014; 8 pages.
International Application No. PCT/US2013/030456; International Search Report and Written Opinion of the International Search Authority, dated Jun. 10, 2013; 11 pages.
Morak, M. et al., "Differential Activity-Based Gel Electrophoresis for Comparative Analysis of Lipolytic and Esterolytic Activities", J. Lipid Res., 50:1281-92, (2009).
Perchiacca, et al., "Structure-Based Design of Conformation-and-Sequence-Specific Antibodies Against Amyloid 3", PNAS, 109(1):84-9, (2012).
Wang, X. et al., "Improved HCP Quantitation by Minimizing Antibody Cross Reactivity to Target Proteins", BioProcess International, 8(1):18-24, (2010).

* cited by examiner

*Primary Examiner* — Gary W Counts
(74) *Attorney, Agent, or Firm* — Dennis A. Bennett

(57) ABSTRACT

This disclosure provides an antibody array for the analysis of the three-dimensional structure of a protein. It includes the development and production of the antibody array and methods of using the array to analyze the three-dimensional structure of a protein as well as to compare the three-dimensional structure of two proteins, for example, a therapeutic protein and a biosimilar, to determine if the two proteins are similar.

17 Claims, 9 Drawing Sheets
Specification includes a Sequence Listing.

Fig. 1. Antibody Titer Determination

Fig. 2. Antibody Specificity

Fig. 5. Variable Region Profile of Seven Marketed mAb Drugs

Fig. 6. Constant Region Profile of Seven Marketed mAb Drugs

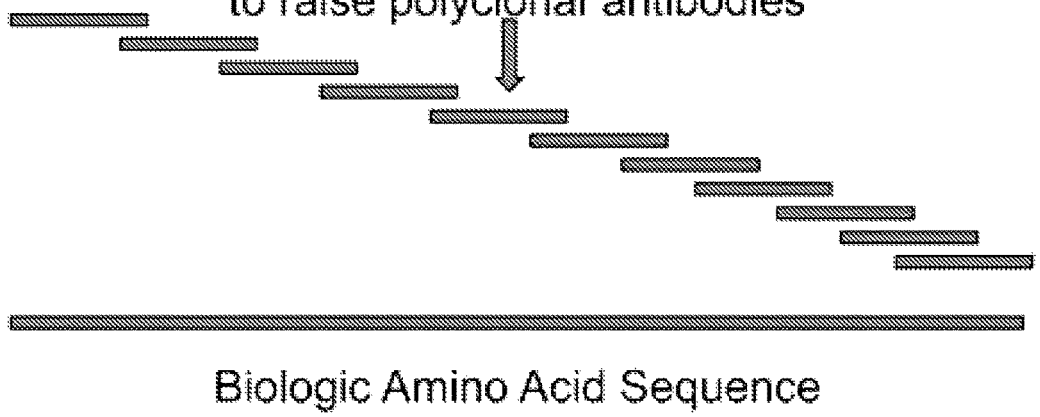
Individual overlapping peptides spanning the biologic are used to raise polyclonal antibodies
Biologic Amino Acid Sequence
Potentially, the entire surface of the biologic is covered by the families of polyclonal antibodies, although in the native biologic the epitopes may be hidden.
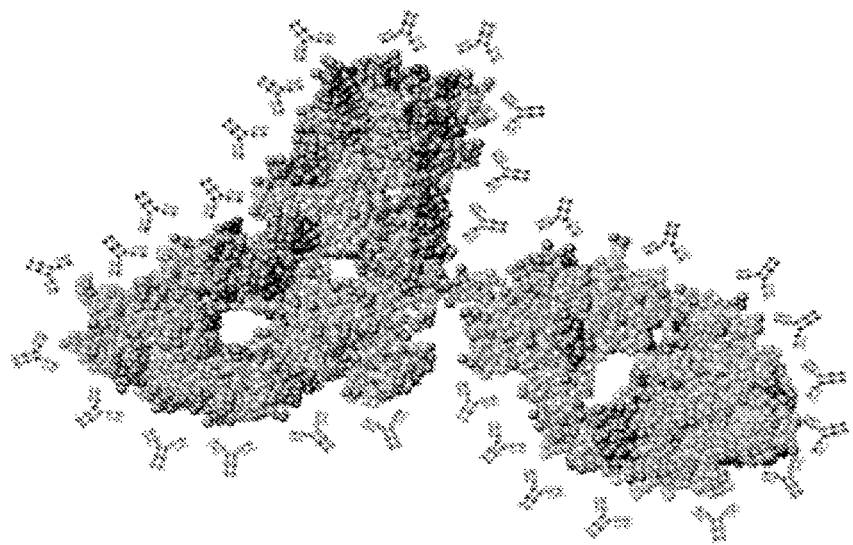
Fig. 8

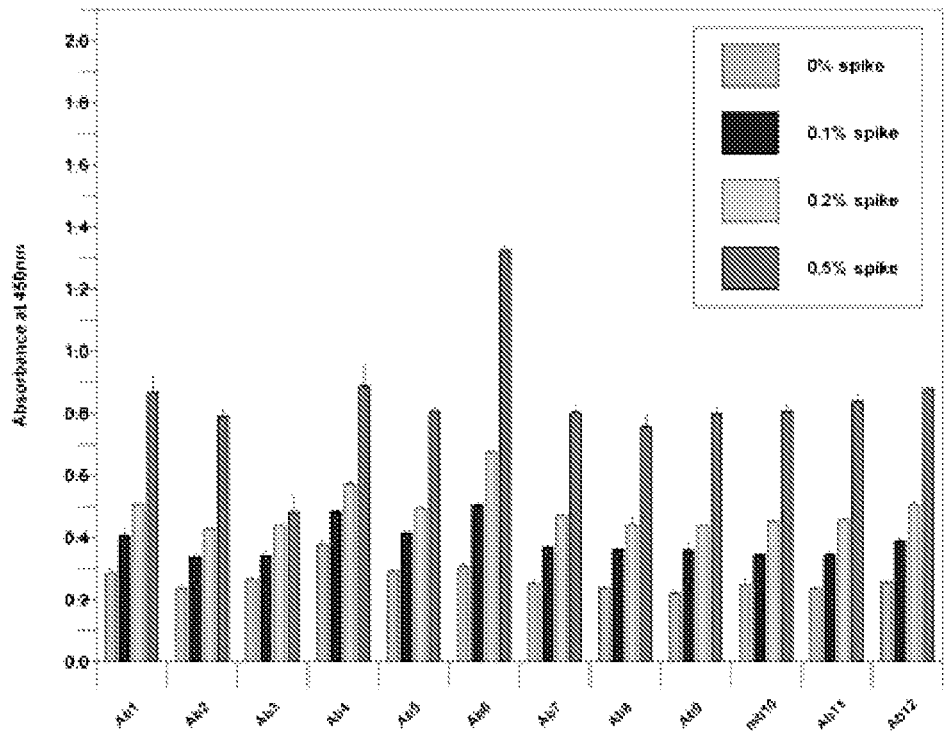
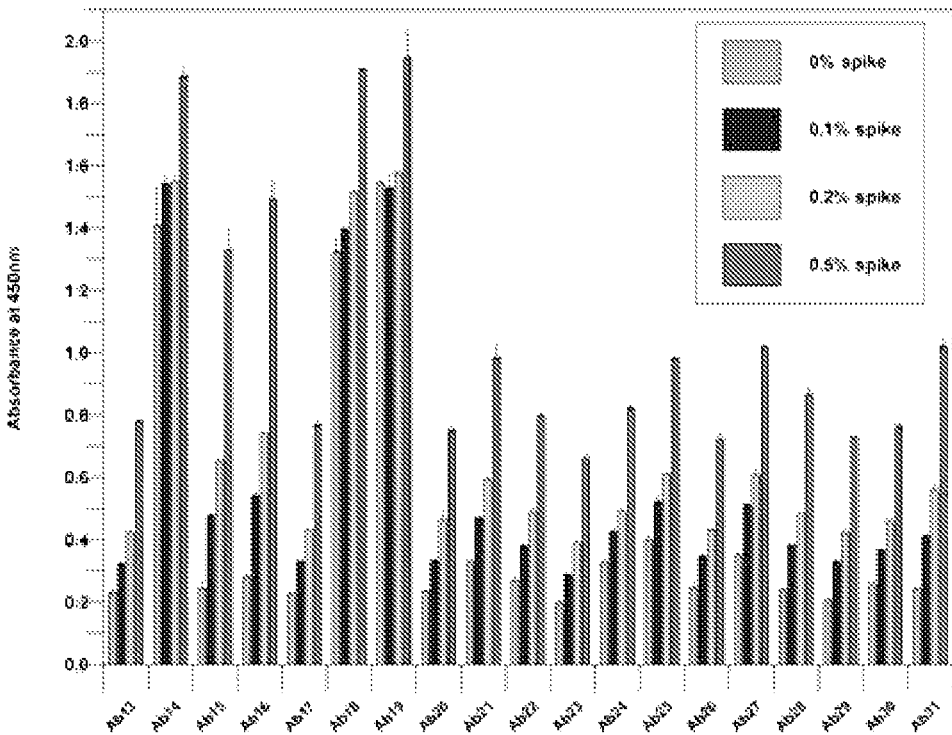
Fig. 9

```
                        SEQUENCE LISTING

<160> NUMBER OF SEQ ID NOS: 108

<210> SEQ ID NO 1
<211> LENGTH: 23
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 2
<211> LENGTH: 27
<212> TYPE: PRT
<213> ORGANISM: Artificial sequence
<220> FEATURE:
<223> OTHER INFORMATION: Antibody array sequence.

<400> SEQUENCE: 2

Cys Gly Gly Arg Val Thr Ile Thr Cys Arg Ala Ser Gln Asp Val Asn
1               5                   10                  15

Thr Ala Val Ala Trp Tyr Gln Gln Lys Pro Gly
            20                  25

<210> SEQ ID NO 3
<211> LENGTH: 29
<212> TYPE: PRT
<213> ORGANISM: Artificial sequence
<220> FEATURE:
<223> OTHER INFORMATION: Antibody array sequence.

<400> SEQUENCE: 3

Cys Gly Gly Gln Gln Lys Pro Gly Lys Ala Pro Lys Leu Leu Ile Tyr
1               5                   10                  15

Ser Ala Ser Phe Leu Tyr Ser Gly Val Pro Ser Arg Phe
            20                  25

<210> SEQ ID NO 4
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 4

Ser Arg Phe Ser Gly Ser Arg Ser Gly Thr Asp Phe Thr Leu Thr Ile
1               5                   10                  15

Ser Ser Leu Gln Pro Glu Asp Phe Ala Thr Tyr Tyr Cys
```

20                  25

<210> SEQ ID NO 5
<211> LENGTH: 24
<212> TYPE: PRT
<213> ORGANISM: Artificial sequence
<220> FEATURE:
<223> OTHER INFORMATION: Antibody array sequence.

<400> SEQUENCE: 5

Cys Gly Gly Phe Ala Thr Tyr Tyr Ser Gln Gln His Tyr Thr Thr Pro
1               5                   10                  15

Pro Thr Phe Gly Gln Gly Thr Lys
            20

<210> SEQ ID NO 6
<211> LENGTH: 24
<212> TYPE: PRT
<213> ORGANISM: Artificial sequence
<220> FEATURE:
<223> OTHER INFORMATION: Antibody array sequence.

<400> SEQUENCE: 6

Cys Gly Gly Thr Lys Val Glu Ile Lys Arg Thr Val Ala Ala Pro Ser
1               5                   10                  15

Val Phe Ile Phe Pro Pro Ser Asp
            20

<210> SEQ ID NO 7
<211> LENGTH: 28
<212> TYPE: PRT
<213> ORGANISM: Artificial sequence
<220> FEATURE:
<223> OTHER INFORMATION: Antibody array sequence.

<400> SEQUENCE: 7

Cys Gly Gly Ile Phe Pro Pro Ser Asp Glu Gln Leu Lys Ser Gly Thr
1               5                   10                  15

Ala Ser Val Val Ser Leu Leu Asn Asn Phe Tyr Pro
            20                  25

<210> SEQ ID NO 8
<211> LENGTH: 22
<212> TYPE: PRT
<213> ORGANISM: Artificial sequence
<220> FEATURE:
<223> OTHER INFORMATION: Antibody array sequence.

<400> SEQUENCE: 8

Cys Leu Leu Asn Asn Phe Tyr Pro Arg Glu Ala Lys Val Gln Trp Lys
1               5                   10                  15

Val Asp Asn Ala Leu Gln
            20

<210> SEQ ID NO 9
<211> LENGTH: 27
<212> TYPE: PRT
<213> ORGANISM: Artificial sequence
<220> FEATURE:
<223> OTHER INFORMATION: Antibody array sequence.

<400> SEQUENCE: 9

Cys Gly Gly Asn Ala Leu Gln Ser Gly Asn Ser Gln Glu Ser Val Thr
1               5                   10                  15

Glu Gln Asp Ser Lys Asp Ser Thr Tyr Ser Leu
            20                  25

<210> SEQ ID NO 10
<211> LENGTH: 30
<212> TYPE: PRT
<213> ORGANISM: Artificial sequence
<220> FEATURE:
<223> OTHER INFORMATION: Antibody array sequence.

<400> SEQUENCE: 10

Cys Gly Gly Lys Asp Ser Thr Tyr Ser Leu Ser Ser Thr Leu Thr Leu
1               5                   10                  15

Ser Lys Ala Asp Tyr Glu Lys His Lys Val Tyr Ala Ser Glu
            20                  25                  30

<210> SEQ ID NO 11
<211> LENGTH: 28
<212> TYPE: PRT
<213> ORGANISM: Artificial sequence
<220> FEATURE:
<223> OTHER INFORMATION: Antibody array sequence.

<400> SEQUENCE: 11

Cys Gly Gly Lys Val Tyr Ala Ser Glu Val Thr His Gln Gly Leu Ser
1               5                   10                  15

Ser Pro Val Thr Lys Ser Phe Asn Arg Gly Glu Ser
            20                  25

<210> SEQ ID NO 12
<211> LENGTH: 24
<212> TYPE: PRT
<213> ORGANISM: Artificial sequence
<220> FEATURE:
<223> OTHER INFORMATION: Antibody array sequence.

<400> SEQUENCE: 12

Cys Gly Gly Glu Val Gln Leu Val Glu Ser Gly Gly Gly Leu Val Gln
1               5                   10                  15

Pro Gly Gly Ser Leu Arg Leu Ser
            20

<210> SEQ ID NO 13
<211> LENGTH: 28
<212> TYPE: PRT
<213> ORGANISM: Artificial sequence
<220> FEATURE:
<223> OTHER INFORMATION: Antibody array sequence.

<400> SEQUENCE: 13

Cys Gly Gly Leu Arg Leu Ser Ser Ala Ala Ser Gly Phe Asn Ile Lys
1               5                   10                  15

Asp Thr Tyr Ile His Trp Val Arg Gln Ala Pro Gly
            20                  25

<210> SEQ ID NO 14
<211> LENGTH: 29
<212> TYPE: PRT
<213> ORGANISM: Artificial sequence
<220> FEATURE:
<223> OTHER INFORMATION: Antibody array sequence.

<400> SEQUENCE: 14

Cys Gly Gly Arg Gln Ala Pro Gly Lys Gly Leu Glu Trp Val Ala Arg
1               5                   10                  15

Ile Tyr Pro Thr Asn Gly Tyr Thr Arg Tyr Ala Asp Ser
            20                  25

<210> SEQ ID NO 15
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (28)..(28)
<223> OTHER INFORMATION: Nle

<400> SEQUENCE: 15

Cys Gly Gly Arg Tyr Ala Asp Ser Val Lys Gly Arg Phe Thr Ile Ser
1               5                   10                  15

Ala Asp Thr Ser Lys Asn Thr Ala Tyr Leu Gln Xaa Asn
            20                  25

<210> SEQ ID NO 16
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (7)..(7)
<223> OTHER INFORMATION: Nle

<400> SEQUENCE: 16

Cys Gly Gly Tyr Leu Gln Xaa Asn Ser Leu Arg Ala Glu Asp Thr Ala
1               5                   10                  15

Val Tyr Tyr Cys Ser Arg Trp Gly Gly Asp Gly Phe Tyr
            20                  25

<210> SEQ ID NO 17
<211> LENGTH: 30
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (9)..(9)
<223> OTHER INFORMATION: Nle

<400> SEQUENCE: 17

Cys Gly Gly Asp Gly Phe Tyr Ala Xaa Asp Tyr Trp Gly Gln Gly Thr
1               5                   10                  15

Leu Val Thr Val Ser Ser Ala Ser Thr Lys Gly Pro Ser Val
            20                  25                  30

<210> SEQ ID NO 18
<211> LENGTH: 28
<212> TYPE: PRT
<213> ORGANISM: Artificial sequence
<220> FEATURE:
<223> OTHER INFORMATION: Antibody array sequence.

<400> SEQUENCE: 18

Cys Gly Gly Pro Ser Val Phe Pro Leu Ala Pro Ser Ser Lys Ser Thr
1               5                   10                  15

Ser Gly Gly Thr Ala Ala Leu Gly Ser Leu Val Lys
            20                  25

```
<210> SEQ ID NO 19
<211> LENGTH: 29
<212> TYPE: PRT
<213> ORGANISM: Artificial sequence
<220> FEATURE:
<223> OTHER INFORMATION: Antibody array sequence.

<400> SEQUENCE: 19

Cys Gly Gly Ser Leu Val Lys Asp Tyr Phe Pro Glu Pro Val Thr Val
1               5                   10                  15

Ser Trp Asn Ser Gly Ala Leu Thr Ser Gly Val His Thr
            20                  25

<210> SEQ ID NO 20
<211> LENGTH: 28
<212> TYPE: PRT
<213> ORGANISM: Artificial sequence
<220> FEATURE:
<223> OTHER INFORMATION: Antibody array sequence.

<400> SEQUENCE: 20

Cys Gly Gly Val His Thr Phe Pro Ala Val Leu Gln Ser Ser Gly Leu
1               5                   10                  15

Tyr Ser Leu Ser Ser Val Val Thr Val Pro Ser Ser
            20                  25

<210> SEQ ID NO 21
<211> LENGTH: 29
<212> TYPE: PRT
<213> ORGANISM: Artificial sequence
<220> FEATURE:
<223> OTHER INFORMATION: Antibody array sequence.

<400> SEQUENCE: 21

Cys Gly Gly Val Thr Val Pro Ser Ser Ser Leu Gly Thr Gln Thr Tyr
1               5                   10                  15

Ile Ser Asn Val Asn His Lys Pro Ser Asn Thr Lys Val
            20                  25

<210> SEQ ID NO 22
<211> LENGTH: 30
<212> TYPE: PRT
<213> ORGANISM: Artificial sequence
<220> FEATURE:
<223> OTHER INFORMATION: Antibody array sequence.

<400> SEQUENCE: 22

Cys Gly Gly Pro Ser Asn Thr Lys Val Asp Lys Val Glu Pro Pro
1               5                   10                  15

Lys Ser Ser Asp Lys Thr His Thr Ser Pro Pro Ser Pro Ala
            20                  25                  30

<210> SEQ ID NO 23
<211> LENGTH: 27
<212> TYPE: PRT
<213> ORGANISM: Artificial sequence
<220> FEATURE:
<223> OTHER INFORMATION: Antibody array sequence.

<400> SEQUENCE: 23

Cys Gly Gly Ser Pro Pro Ser Pro Ala Pro Glu Leu Leu Gly Gly Pro
1               5                   10                  15

Ser Val Phe Leu Phe Pro Pro Lys Pro Lys Asp
            20                  25
```

-continued

```
              20                  25

<210> SEQ ID NO 24
<211> LENGTH: 25
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (17)..(17)
<223> OTHER INFORMATION: Nle

<400> SEQUENCE: 24

Cys Gly Gly Ser Val Phe Leu Phe Pro Pro Lys Pro Lys Asp Thr Leu
1               5                   10                  15

Xaa Ile Ser Arg Thr Pro Glu Val Thr
            20                  25

<210> SEQ ID NO 25
<211> LENGTH: 25
<212> TYPE: PRT
<213> ORGANISM: Artificial sequence
<220> FEATURE:
<223> OTHER INFORMATION: Antibody array sequence.

<400> SEQUENCE: 25

Cys Gly Gly Pro Glu Val Thr Cys Val Val Val Asp Val Ser His Glu
1               5                   10                  15

Asp Pro Glu Val Lys Phe Asn Trp Tyr
            20                  25

<210> SEQ ID NO 26
<211> LENGTH: 29
<212> TYPE: PRT
<213> ORGANISM: Artificial sequence
<220> FEATURE:
<223> OTHER INFORMATION: Antibody array sequence.

<400> SEQUENCE: 26

Cys Gly Gly Val Lys Phe Asn Trp Tyr Val Asp Gly Val Glu Val His
1               5                   10                  15

Asn Ala Lys Thr Lys Pro Arg Glu Glu Gln Tyr Asn Ser
            20                  25

<210> SEQ ID NO 27
<211> LENGTH: 29
<212> TYPE: PRT
<213> ORGANISM: Artificial sequence
<220> FEATURE:
<223> OTHER INFORMATION: Antibody array sequence.

<400> SEQUENCE: 27

Cys Gly Gly Gln Tyr Asn Ser Thr Tyr Arg Val Val Ser Val Leu Thr
1               5                   10                  15

Val Leu His Gln Asp Trp Leu Asn Gly Lys Glu Tyr Lys
            20                  25

<210> SEQ ID NO 28
<211> LENGTH: 30
<212> TYPE: PRT
<213> ORGANISM: Artificial sequence
<220> FEATURE:
<223> OTHER INFORMATION: Antibody array sequence.

<400> SEQUENCE: 28
```

Cys Gly Gly Lys Glu Tyr Lys Ser Lys Val Ser Asn Lys Ala Leu Pro
1               5                   10                  15

Ala Pro Ile Glu Lys Thr Ile Ser Lys Ala Lys Gly Gln Pro
            20                  25                  30

<210> SEQ ID NO 29
<211> LENGTH: 28
<212> TYPE: PRT
<213> ORGANISM: Artificial sequence
<220> FEATURE:
<223> OTHER INFORMATION: Antibody array sequence.

<400> SEQUENCE: 29

Cys Gly Gly Lys Gly Gln Pro Arg Glu Pro Gln Val Tyr Thr Leu Pro
1               5                   10                  15

Pro Ser Arg Asp Glu Leu Thr Lys Asn Gln Val Ser
            20                  25

<210> SEQ ID NO 30
<211> LENGTH: 29
<212> TYPE: PRT
<213> ORGANISM: Artificial sequence
<220> FEATURE:
<223> OTHER INFORMATION: Antibody array sequence.

<400> SEQUENCE: 30

Cys Gly Gly Lys Asn Gln Val Ser Leu Thr Ser Leu Val Lys Gly Phe
1               5                   10                  15

Tyr Pro Ser Asp Ile Ala Val Glu Trp Glu Ser Asn Gly
            20                  25

<210> SEQ ID NO 31
<211> LENGTH: 27
<212> TYPE: PRT
<213> ORGANISM: Artificial sequence
<220> FEATURE:
<223> OTHER INFORMATION: Antibody array sequence.

<400> SEQUENCE: 31

Cys Gly Gly Trp Glu Ser Asn Gly Gln Pro Glu Asn Asn Tyr Lys Thr
1               5                   10                  15

Thr Pro Pro Val Leu Asp Ser Asp Gly Ser Phe
            20                  25

<210> SEQ ID NO 32
<211> LENGTH: 28
<212> TYPE: PRT
<213> ORGANISM: Artificial sequence
<220> FEATURE:
<223> OTHER INFORMATION: Antibody array sequence.

<400> SEQUENCE: 32

Cys Gly Gly Ser Asp Gly Ser Phe Phe Leu Tyr Ser Lys Leu Thr Val
1               5                   10                  15

Asp Lys Ser Arg Trp Gln Gln Gly Asn Val Phe Ser
            20                  25

<210> SEQ ID NO 33
<211> LENGTH: 30
<212> TYPE: PRT
<213> ORGANISM: Artificial sequence
<220> FEATURE:
<223> OTHER INFORMATION: Antibody array sequence.
<220> FEATURE:

```
<221> NAME/KEY: MOD_RES
<222> LOCATION: (11)..(11)
<223> OTHER INFORMATION: Nle

<400> SEQUENCE: 33

Cys Gly Gly Asn Val Phe Ser Ser Val Xaa His Glu Ala Leu His
1               5                   10                  15

Asn His Tyr Thr Gln Lys Ser Leu Ser Leu Ser Pro Gly Lys
            20                  25                  30

<210> SEQ ID NO 34
<211> LENGTH: 23
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: Nle

<400> SEQUENCE: 34

Gln Ile Val Leu Ser Gln Ser Pro Ala Ile Leu Ser Ala Ser Pro Gly
1               5                   10                  15

Glu Lys Val Thr Xaa Thr Cys
            20

<210> SEQ ID NO 35
<211> LENGTH: 26
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (18)..(18)
<223> OTHER INFORMATION: Nle

<400> SEQUENCE: 35

Cys Gly Gly Lys Val Thr Xaa Thr Ser Arg Ala Ser Ser Ser Val Ser
1               5                   10                  15

Tyr Xaa His Trp Tyr Gln Gln Lys Pro Gly
            20                  25

<210> SEQ ID NO 36
<211> LENGTH: 29
<212> TYPE: PRT
<213> ORGANISM: Artificial sequence
<220> FEATURE:
<223> OTHER INFORMATION: Antibody array sequence.

<400> SEQUENCE: 36

Cys Gly Gly Gln Gln Lys Pro Gly Ser Ser Pro Lys Pro Trp Ile Tyr
1               5                   10                  15

Ala Pro Ser Asn Leu Ala Ser Gly Val Pro Ala Arg Phe
            20                  25

<210> SEQ ID NO 37
<211> LENGTH: 29
```

```
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 37

Ala Arg Phe Ser Gly Ser Gly Ser Gly Thr Ser Tyr Ser Leu Thr Ile
1               5                   10                  15

Ser Arg Val Glu Ala Glu Asp Ala Ala Thr Tyr Tyr Cys
            20                  25

<210> SEQ ID NO 38
<211> LENGTH: 24
<212> TYPE: PRT
<213> ORGANISM: Artificial sequence
<220> FEATURE:
<223> OTHER INFORMATION: Antibody array sequence.

<400> SEQUENCE: 38

Cys Gly Gly Ala Ala Thr Tyr Tyr Ser Gln Gln Trp Ser Phe Asn Pro
1               5                   10                  15

Pro Thr Phe Gly Ala Gly Thr Lys
            20

<210> SEQ ID NO 39
<211> LENGTH: 26
<212> TYPE: PRT
<213> ORGANISM: Artificial sequence
<220> FEATURE:
<223> OTHER INFORMATION: Antibody array sequence.

<400> SEQUENCE: 39

Cys Gly Gly Ala Gly Thr Lys Leu Glu Leu Lys Arg Thr Val Ala Ala
1               5                   10                  15

Pro Ser Val Phe Ile Phe Pro Pro Ser Asp
            20                  25

<210> SEQ ID NO 40
<211> LENGTH: 24
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (23)..(23)
<223> OTHER INFORMATION: Nle

<400> SEQUENCE: 40

Cys Gly Gly Gln Ala Tyr Leu Gln Gln Ser Gly Ala Glu Leu Val Arg
1               5                   10                  15

Pro Gly Ala Ser Val Lys Xaa Ser
            20

<210> SEQ ID NO 41
<211> LENGTH: 28
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (6)..(6)
```

```
<223> OTHER INFORMATION: Nle
<220> FEATURE:
<221> NAME/KEY: MOD_RES
<222> LOCATION: (20)..(20)
<223> OTHER INFORMATION: Nle

<400> SEQUENCE: 41

Cys Gly Gly Val Lys Xaa Ser Cys Lys Ala Ser Gly Tyr Thr Phe Thr
1               5                   10                  15

Ser Tyr Asn Xaa His Trp Val Lys Gln Thr Pro Arg
            20                  25

<210> SEQ ID NO 42
<211> LENGTH: 29
<212> TYPE: PRT
<213> ORGANISM: Artificial sequence
<220> FEATURE:
<223> OTHER INFORMATION: Antibody array sequence.

<400> SEQUENCE: 42

Cys Gly Gly Lys Gln Thr Pro Arg Gln Gly Leu Glu Trp Ile Gly Ala
1               5                   10                  15

Ile Tyr Pro Gly Asn Gly Asp Thr Ser Tyr Asn Gln Lys
            20                  25

<210> SEQ ID NO 43
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (26)..(26)
<223> OTHER INFORMATION: Nle

<400> SEQUENCE: 43

Cys Gly Gly Ser Tyr Asn Gln Lys Phe Lys Gly Lys Ala Thr Leu Thr
1               5                   10                  15

Val Asp Lys Ser Ser Ser Thr Ala Tyr Xaa Gln Leu Ser
            20                  25

<210> SEQ ID NO 44
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (5)..(5)
<223> OTHER INFORMATION: Nle

<400> SEQUENCE: 44

Cys Gly Gly Tyr Xaa Gln Leu Ser Ser Leu Thr Ser Glu Asp Ser Ala
1               5                   10                  15

Val Tyr Phe Ser Ala Arg Val Val Tyr Tyr Ser Asn Ser
            20                  25

<210> SEQ ID NO 45
<211> LENGTH: 28
<212> TYPE: PRT
<213> ORGANISM: Artificial sequence
<220> FEATURE:
<223> OTHER INFORMATION: Antibody array sequence.

<400> SEQUENCE: 45
```

Cys Gly Gly Tyr Tyr Ser Asn Ser Tyr Trp Tyr Phe Asp Val Trp Gly
1               5                   10                  15

Thr Gly Thr Thr Val Thr Val Ser Gly Pro Ser Val
            20                  25

<210> SEQ ID NO 46
<211> LENGTH: 27
<212> TYPE: PRT
<213> ORGANISM: Artificial sequence
<220> FEATURE:
<223> OTHER INFORMATION: Antibody array sequence.

<400> SEQUENCE: 46

Cys Gly Gly Arg Val Thr Ile Thr Ser Ser Ala Ser Gln Asp Ile Ser
1               5                   10                  15

Asn Tyr Leu Asn Trp Tyr Gln Gln Lys Pro Gly
            20                  25

<210> SEQ ID NO 47
<211> LENGTH: 29
<212> TYPE: PRT
<213> ORGANISM: Artificial sequence
<220> FEATURE:
<223> OTHER INFORMATION: Antibody array sequence.

<400> SEQUENCE: 47

Cys Gly Gly Gln Gln Lys Pro Gly Lys Ala Pro Lys Val Leu Ile Tyr
1               5                   10                  15

Phe Thr Ser Ser Leu His Ser Gly Val Pro Ser Arg Phe
            20                  25

<210> SEQ ID NO 48
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 48

Ser Arg Phe Ser Gly Ser Gly Ser Gly Thr Asp Phe Thr Leu Thr Ile
1               5                   10                  15

Ser Ser Leu Gln Pro Glu Asp Phe Ala Thr Tyr Tyr Cys
            20                  25

<210> SEQ ID NO 49
<211> LENGTH: 24
<212> TYPE: PRT
<213> ORGANISM: Artificial sequence
<220> FEATURE:
<223> OTHER INFORMATION: Antibody array sequence.

<400> SEQUENCE: 49

Cys Gly Gly Phe Ala Thr Tyr Tyr Ser Gln Gln Tyr Ser Thr Val Pro
1               5                   10                  15

Trp Thr Phe Gly Gln Gly Thr Lys
            20

<210> SEQ ID NO 50
<211> LENGTH: 28
<212> TYPE: PRT

```
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (20)..(20)
<223> OTHER INFORMATION: Nle

<400> SEQUENCE: 50

Cys Gly Gly Leu Arg Leu Ser Ser Ala Ala Ser Gly Tyr Thr Phe Thr
1               5                   10                  15

Asn Tyr Gly Xaa Asn Trp Val Arg Gln Ala Pro Gly
            20                  25

<210> SEQ ID NO 51
<211> LENGTH: 29
<212> TYPE: PRT
<213> ORGANISM: Artificial sequence
<220> FEATURE:
<223> OTHER INFORMATION: Antibody array sequence.

<400> SEQUENCE: 51

Cys Gly Gly Arg Gln Ala Pro Gly Lys Gly Leu Glu Trp Val Gly Trp
1               5                   10                  15

Ile Asn Thr Tyr Thr Gly Glu Pro Thr Tyr Ala Ala Asp
            20                  25

<210> SEQ ID NO 52
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (28)..(28)
<223> OTHER INFORMATION: Nle

<400> SEQUENCE: 52

Cys Gly Gly Thr Tyr Ala Ala Asp Phe Lys Arg Arg Phe Thr Phe Ser
1               5                   10                  15

Leu Asp Thr Ser Lys Ser Thr Ala Tyr Leu Gln Xaa Asn
            20                  25

<210> SEQ ID NO 53
<211> LENGTH: 30
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (7)..(7)
<223> OTHER INFORMATION: Nle

<400> SEQUENCE: 53

Cys Gly Gly Tyr Leu Gln Xaa Asn Ser Leu Arg Ala Glu Asp Thr Ala
1               5                   10                  15

Val Tyr Tyr Ser Ala Lys Tyr Pro His Tyr Tyr Gly Ser Ser
            20                  25                  30

<210> SEQ ID NO 54
<211> LENGTH: 30
<212> TYPE: PRT
<213> ORGANISM: Artificial sequence
<220> FEATURE:
<223> OTHER INFORMATION: Antibody array sequence.
```

```
<400> SEQUENCE: 54

Cys Gly Gly Tyr Tyr Gly Ser Ser His Trp Tyr Phe Asp Val Trp Gly
1               5                   10                  15

Gln Gly Thr Leu Val Thr Val Ser Ser Ala Ser Thr Lys Gly
            20                  25                  30

<210> SEQ ID NO 55
<211> LENGTH: 24
<212> TYPE: PRT
<213> ORGANISM: Artificial sequence
<220> FEATURE:
<223> OTHER INFORMATION: Antibody array sequence.

<400> SEQUENCE: 55

Cys Gly Gly Arg Val Thr Ile Thr Ser Arg Ala Ser Gln Gly Ile Arg
1               5                   10                  15

Asn Tyr Leu Ala Trp Tyr Gln Gln
            20

<210> SEQ ID NO 56
<211> LENGTH: 30
<212> TYPE: PRT
<213> ORGANISM: Artificial sequence
<220> FEATURE:
<223> OTHER INFORMATION: Antibody array sequence.

<400> SEQUENCE: 56

Cys Gly Gly Gln Gln Lys Pro Gly Lys Ala Pro Lys Leu Leu Ile Tyr
1               5                   10                  15

Ala Ala Ser Thr Leu Gln Ser Gly Val Pro Ser Arg Phe Ser
            20                  25                  30

<210> SEQ ID NO 57
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 57

Ser Arg Phe Ser Gly Ser Gly Ser Gly Thr Asp Phe Thr Leu Thr Ile
1               5                   10                  15

Ser Ser Leu Gln Pro Glu Asp Val Ala Thr Tyr Tyr Cys
            20                  25

<210> SEQ ID NO 58
<211> LENGTH: 24
<212> TYPE: PRT
<213> ORGANISM: Artificial sequence
<220> FEATURE:
<223> OTHER INFORMATION: Antibody array sequence.

<400> SEQUENCE: 58

Cys Gly Gly Val Ala Thr Tyr Tyr Ser Gln Arg Tyr Asn Arg Ala Pro
1               5                   10                  15

Tyr Thr Phe Gly Gln Gly Thr Lys
            20

<210> SEQ ID NO 59
```

```
<211> LENGTH: 22
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 59

Glu Val Gln Leu Val Glu Ser Gly Gly Gly Leu Val Gln Pro Gly Arg
1               5                   10                  15

Ser Leu Arg Leu Ser Cys
            20

<210> SEQ ID NO 60
<211> LENGTH: 28
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (20)..(20)
<223> OTHER INFORMATION: Nle

<400> SEQUENCE: 60

Cys Gly Gly Leu Arg Leu Ser Ser Ala Ala Ser Gly Phe Thr Phe Asp
1               5                   10                  15

Asp Tyr Ala Xaa His Trp Val Arg Gln Ala Pro Gly
            20                  25

<210> SEQ ID NO 61
<211> LENGTH: 29
<212> TYPE: PRT
<213> ORGANISM: Artificial sequence
<220> FEATURE:
<223> OTHER INFORMATION: Antibody array sequence.

<400> SEQUENCE: 61

Cys Gly Gly Arg Gln Ala Pro Gly Lys Gly Leu Glu Trp Val Ser Ala
1               5                   10                  15

Ile Thr Trp Asn Ser Gly His Ile Asp Tyr Ala Asp Ser
            20                  25

<210> SEQ ID NO 62
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (28)..(28)
<223> OTHER INFORMATION: Nle

<400> SEQUENCE: 62

Cys Gly Gly Asp Tyr Ala Asp Ser Val Glu Gly Arg Phe Thr Ile Ser
1               5                   10                  15

Arg Asp Asn Ala Lys Asn Ser Leu Tyr Leu Gln Xaa Asn
            20                  25

<210> SEQ ID NO 63
<211> LENGTH: 30
<212> TYPE: PRT
<213> ORGANISM: Artificial sequence
```

```
<220> FEATURE:
<223> OTHER INFORMATION: Antibody array sequence.
<220> FEATURE:
<221> NAME/KEY: MOD_RES
<222> LOCATION: (7)..(7)
<223> OTHER INFORMATION: Nle

<400> SEQUENCE: 63

Cys Gly Gly Tyr Leu Gln Xaa Asn Ser Leu Arg Ala Glu Asp Thr Ala
1               5                   10                  15

Val Tyr Tyr Ser Ala Lys Val Ser Tyr Leu Ser Thr Ala Ser
            20                  25                  30

<210> SEQ ID NO 64
<211> LENGTH: 30
<212> TYPE: PRT
<213> ORGANISM: Artificial sequence
<220> FEATURE:
<223> OTHER INFORMATION: Antibody array sequence.

<400> SEQUENCE: 64

Cys Gly Gly Leu Ser Thr Ala Ser Ser Leu Asp Tyr Trp Gly Gln Gly
1               5                   10                  15

Thr Leu Val Thr Val Ser Ser Ala Ser Thr Lys Gly Pro Ser
            20                  25                  30

<210> SEQ ID NO 65
<211> LENGTH: 23
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 65

Asp Ile Leu Leu Thr Gln Ser Pro Val Ile Leu Ser Val Ser Pro Gly
1               5                   10                  15

Glu Arg Val Ser Phe Ser Cys
            20

<210> SEQ ID NO 66
<211> LENGTH: 27
<212> TYPE: PRT
<213> ORGANISM: Artificial sequence
<220> FEATURE:
<223> OTHER INFORMATION: Antibody array sequence.

<400> SEQUENCE: 66

Cys Gly Gly Arg Val Ser Phe Ser Ser Arg Ala Ser Gln Ser Ile Gly
1               5                   10                  15

Thr Asn Ile His Trp Tyr Gln Gln Arg Thr Asn
            20                  25

<210> SEQ ID NO 67
<211> LENGTH: 29
<212> TYPE: PRT
<213> ORGANISM: Artificial sequence
<220> FEATURE:
<223> OTHER INFORMATION: Antibody array sequence.

<400> SEQUENCE: 67

Cys Gly Gly Gln Gln Arg Thr Asn Gly Ser Pro Arg Leu Leu Ile Lys
1               5                   10                  15
```

```
Tyr Ala Ser Glu Ser Ile Ser Gly Ile Pro Ser Arg Phe
            20                  25

<210> SEQ ID NO 68
<211> LENGTH: 30
<212> TYPE: PRT
<213> ORGANISM: Artificial sequence
<220> FEATURE:
<223> OTHER INFORMATION: Antibody array sequence.

<400> SEQUENCE: 68

Cys Gly Gly Ser Arg Phe Ser Gly Ser Gly Ser Gly Thr Asp Phe Thr
1               5                   10                  15

Leu Ser Ile Asn Ser Val Glu Ser Glu Asp Ile Ala Asp Tyr
            20                  25                  30

<210> SEQ ID NO 69
<211> LENGTH: 24
<212> TYPE: PRT
<213> ORGANISM: Artificial sequence
<220> FEATURE:
<223> OTHER INFORMATION: Antibody array sequence.

<400> SEQUENCE: 69

Cys Gly Gly Ile Ala Asp Tyr Tyr Ser Gln Gln Asn Asn Trp Pro
1               5                   10                  15

Thr Thr Phe Gly Ala Gly Thr Lys
            20

<210> SEQ ID NO 70
<211> LENGTH: 22
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 70

Gln Val Gln Leu Lys Gln Ser Gly Pro Gly Leu Val Gln Pro Ser Gln
1               5                   10                  15

Ser Leu Ser Ile Thr Cys
            20

<210> SEQ ID NO 71
<211> LENGTH: 28
<212> TYPE: PRT
<213> ORGANISM: Artificial sequence
<220> FEATURE:
<223> OTHER INFORMATION: Antibody array sequence.

<400> SEQUENCE: 71

Cys Gly Gly Leu Ser Ile Thr Ser Thr Val Ser Gly Phe Ser Leu Thr
1               5                   10                  15

Asn Tyr Gly Val His Trp Val Arg Gln Ser Pro Gly
            20                  25

<210> SEQ ID NO 72
<211> LENGTH: 28
<212> TYPE: PRT
<213> ORGANISM: Artificial sequence
<220> FEATURE:
<223> OTHER INFORMATION: Antibody array sequence.
```

<400> SEQUENCE: 72

Cys Gly Gly Arg Gln Ser Pro Gly Lys Gly Leu Glu Trp Leu Gly Val
1               5                   10                  15

Ile Trp Ser Gly Gly Asn Thr Asp Tyr Asn Thr Pro
            20                  25

<210> SEQ ID NO 73
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (28)..(28)
<223> OTHER INFORMATION: Nle

<400> SEQUENCE: 73

Cys Gly Gly Asp Tyr Asn Thr Pro Phe Thr Ser Arg Leu Ser Ile Asn
1               5                   10                  15

Lys Asp Asn Ser Lys Ser Gln Val Phe Phe Lys Xaa Asn
            20                  25

<210> SEQ ID NO 74
<211> LENGTH: 27
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (7)..(7)
<223> OTHER INFORMATION: Nle

<400> SEQUENCE: 74

Cys Gly Gly Phe Phe Lys Xaa Asn Ser Leu Gln Ser Asn Asp Thr Ala
1               5                   10                  15

Ile Tyr Tyr Ser Ala Arg Ala Leu Thr Tyr Tyr
            20                  25

<210> SEQ ID NO 75
<211> LENGTH: 30
<212> TYPE: PRT
<213> ORGANISM: Artificial sequence
<220> FEATURE:
<223> OTHER INFORMATION: Antibody array sequence.

<400> SEQUENCE: 75

Cys Gly Gly Ala Leu Thr Tyr Tyr Asp Tyr Glu Phe Ala Tyr Trp Gly
1               5                   10                  15

Gln Gly Thr Leu Val Thr Val Ser Ala Ala Ser Thr Lys Gly
            20                  25                  30

<210> SEQ ID NO 76
<211> LENGTH: 27
<212> TYPE: PRT
<213> ORGANISM: Artificial sequence
<220> FEATURE:
<223> OTHER INFORMATION: Antibody array sequence.

<400> SEQUENCE: 76

Cys Gly Gly Arg Val Thr Ile Thr Ser Lys Ala Ser Gln Asn Ile Asp
1               5                   10                  15

Lys Tyr Leu Asn Trp Tyr Gln Gln Lys Pro Gly 20                  25

<210> SEQ ID NO 77
<211> LENGTH: 29
<212> TYPE: PRT
<213> ORGANISM: Artificial sequence
<220> FEATURE:
<223> OTHER INFORMATION: Antibody array sequence.

<400> SEQUENCE: 77

Cys Gly Gly Gln Gln Lys Pro Gly Lys Ala Pro Lys Leu Leu Ile Tyr
1               5                   10                  15

Asn Thr Asn Asn Leu Gln Thr Gly Val Pro Ser Arg Phe
            20                  25

<210> SEQ ID NO 78
<211> LENGTH: 30
<212> TYPE: PRT
<213> ORGANISM: Artificial sequence
<220> FEATURE:
<223> OTHER INFORMATION: Antibody array sequence.

<400> SEQUENCE: 78

Cys Gly Gly Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr
            20                  25                  30

<210> SEQ ID NO 79
<211> LENGTH: 24
<212> TYPE: PRT
<213> ORGANISM: Artificial sequence
<220> FEATURE:
<223> OTHER INFORMATION: Antibody array sequence.

<400> SEQUENCE: 79

Cys Gly Gly Ile Ala Thr Tyr Tyr Ser Leu Gln His Ile Ser Arg Pro
1               5                   10                  15

Arg Thr Phe Gly Gln Gly Thr Lys
            20

<210> SEQ ID NO 80
<211> LENGTH: 26
<212> TYPE: PRT
<213> ORGANISM: Artificial sequence
<220> FEATURE:
<223> OTHER INFORMATION: Antibody array sequence.

<400> SEQUENCE: 80

Cys Gly Gly Gln Gly Thr Lys Val Glu Ile Lys Arg Thr Val Ala Ala
1               5                   10                  15

Pro Ser Val Phe Ile Phe Pro Pro Ser Asp
            20                  25

<210> SEQ ID NO 81
<211> LENGTH: 22
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 81

```
Gln Val Gln Leu Gln Glu Ser Gly Pro Gly Leu Val Arg Pro Ser Gln
1               5                   10                  15

Thr Leu Ser Leu Thr Cys
            20
```

<210> SEQ ID NO 82
<211> LENGTH: 28
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (20)..(20)
<223> OTHER INFORMATION: Nle

<400> SEQUENCE: 82

```
Cys Gly Gly Leu Ser Leu Thr Ser Thr Val Ser Gly Phe Thr Phe Thr
1               5                   10                  15

Asp Phe Tyr Xaa Asn Trp Val Arg Gln Pro Pro Gly
            20                  25
```

<210> SEQ ID NO 83
<211> LENGTH: 30
<212> TYPE: PRT
<213> ORGANISM: Artificial sequence
<220> FEATURE:
<223> OTHER INFORMATION: Antibody array sequence.

<400> SEQUENCE: 83

```
Cys Gly Gly Arg Gln Pro Pro Gly Arg Gly Leu Glu Trp Ile Gly Phe
1               5                   10                  15

Ile Arg Asp Lys Ala Lys Gly Tyr Thr Thr Glu Tyr Asn Pro
            20                  25                  30
```

<210> SEQ ID NO 84
<211> LENGTH: 29
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (15)..(15)
<223> OTHER INFORMATION: Nle

<400> SEQUENCE: 84

```
Cys Gly Gly Glu Tyr Asn Pro Ser Val Lys Gly Arg Val Thr Xaa Leu
1               5                   10                  15

Val Asp Thr Ser Lys Asn Gln Phe Ser Leu Arg Leu Ser
            20                  25
```

<210> SEQ ID NO 85
<211> LENGTH: 29
<212> TYPE: PRT
<213> ORGANISM: Artificial sequence
<220> FEATURE:
<223> OTHER INFORMATION: Antibody array sequence.

<400> SEQUENCE: 85

```
Cys Gly Gly Ser Leu Arg Leu Ser Ser Val Thr Ala Ala Asp Thr Ala
1               5                   10                  15

Val Tyr Tyr Ser Ala Arg Glu Gly His Thr Ala Ala Pro
            20                  25
```

```
<210> SEQ ID NO 86
<211> LENGTH: 30
<212> TYPE: PRT
<213> ORGANISM: Artificial sequence
<220> FEATURE:
<223> OTHER INFORMATION: Antibody array sequence.

<400> SEQUENCE: 86

Cys Gly Gly His Thr Ala Ala Pro Phe Asp Tyr Trp Gly Gln Gly Ser
1               5                   10                  15

Leu Val Thr Val Ser Ser Ala Ser Thr Lys Gly Pro Ser Val
            20                  25                  30

<210> SEQ ID NO 87
<211> LENGTH: 23
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle

<400> SEQUENCE: 87

Asp Ile Gln Xaa Thr Gln Ser Pro Ser Thr Leu Ser Ala Ser Val Gly
1               5                   10                  15

Asp Arg Val Thr Ile Thr Cys
            20

<210> SEQ ID NO 88
<211> LENGTH: 26
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (18)..(18)
<223> OTHER INFORMATION: Nle

<400> SEQUENCE: 88

Cys Gly Gly Arg Val Thr Ile Thr Ser Lys Ser Gln Leu Ser Val Gly
1               5                   10                  15

Tyr Xaa His Trp Tyr Gln Gln Lys Pro Gly
            20                  25

<210> SEQ ID NO 89
<211> LENGTH: 29
<212> TYPE: PRT
<213> ORGANISM: Artificial sequence
<220> FEATURE:
<223> OTHER INFORMATION: Antibody array sequence.

<400> SEQUENCE: 89

Cys Gly Gly Gln Gln Lys Pro Gly Lys Ala Pro Lys Leu Leu Ile Tyr
1               5                   10                  15

Asp Thr Ser Lys Leu Ala Ser Gly Val Pro Ser Arg Phe
            20                  25

<210> SEQ ID NO 90
<211> LENGTH: 30
```

```
<212> TYPE: PRT
<213> ORGANISM: Artificial sequence
<220> FEATURE:
<223> OTHER INFORMATION: Antibody array sequence.

<400> SEQUENCE: 90

Cys Gly Gly Ser Arg Phe Ser Gly Ser Gly Ser Gly Thr Ala Phe Thr
1               5                   10                  15

Leu Thr Ile Ser Ser Leu Gln Pro Asp Asp Phe Ala Thr Tyr
            20                  25                  30

<210> SEQ ID NO 91
<211> LENGTH: 24
<212> TYPE: PRT
<213> ORGANISM: Artificial sequence
<220> FEATURE:
<223> OTHER INFORMATION: Antibody array sequence.

<400> SEQUENCE: 91

Cys Gly Gly Phe Ala Thr Tyr Tyr Ser Phe Gln Gly Ser Gly Tyr Pro
1               5                   10                  15

Phe Thr Phe Gly Gly Gly Thr Lys
            20

<210> SEQ ID NO 92
<211> LENGTH: 24
<212> TYPE: PRT
<213> ORGANISM: Artificial sequence
<220> FEATURE:
<223> OTHER INFORMATION: Antibody array sequence.

<400> SEQUENCE: 92

Cys Gly Gly Thr Lys Leu Glu Ile Lys Arg Thr Val Ala Ala Pro Ser
1               5                   10                  15

Val Phe Ile Phe Pro Pro Ser Asp
            20

<210> SEQ ID NO 93
<211> LENGTH: 22
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 93

Gln Val Thr Leu Arg Glu Ser Gly Pro Ala Leu Val Lys Pro Thr Gln
1               5                   10                  15

Thr Leu Thr Leu Thr Cys
            20

<210> SEQ ID NO 94
<211> LENGTH: 30
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (20)..(20)
<223> OTHER INFORMATION: Nle

<400> SEQUENCE: 94
```

-continued

```
Cys Gly Gly Leu Thr Leu Thr Ser Thr Phe Ser Gly Phe Ser Leu Ser
1               5                   10                  15

Thr Ser Gly Xaa Ser Val Gly Trp Ile Arg Gln Pro Pro Gly
            20                  25                  30
```

<210> SEQ ID NO 95
<211> LENGTH: 28
<212> TYPE: PRT
<213> ORGANISM: Artificial sequence
<220> FEATURE:
<223> OTHER INFORMATION: Antibody array sequence.

<400> SEQUENCE: 95

```
Cys Gly Gly Arg Gln Pro Pro Gly Lys Ala Leu Glu Trp Leu Ala Asp
1               5                   10                  15

Ile Trp Trp Asp Asp Lys Lys Asp Tyr Asn Pro Ser
            20                  25
```

<210> SEQ ID NO 96
<211> LENGTH: 29
<212> TYPE: PRT
<213> ORGANISM: Artificial sequence
<220> FEATURE:
<223> OTHER INFORMATION: Antibody array sequence.

<400> SEQUENCE: 96

```
Cys Gly Gly Asp Tyr Asn Pro Ser Leu Lys Ser Arg Leu Thr Ile Ser
1               5                   10                  15

Lys Asp Thr Ser Ala Asn Gln Val Val Leu Lys Val Thr
            20                  25
```

<210> SEQ ID NO 97
<211> LENGTH: 26
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (24)..(24)
<223> OTHER INFORMATION: Nle

<400> SEQUENCE: 97

```
Cys Gly Gly Val Leu Lys Val Thr Asn Xaa Asp Pro Ala Asp Thr Ala
1               5                   10                  15

Thr Tyr Tyr Ser Ala Arg Ser Xaa Ile Thr
            20                  25
```

<210> SEQ ID NO 98
<211> LENGTH: 30
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (5)..(5)
<223> OTHER INFORMATION: Nle

<400> SEQUENCE: 98

```
Cys Gly Gly Ser Xaa Ile Thr Asn Trp Tyr Phe Asp Val Trp Gly Ala
1               5                   10                  15
```

Gly Thr Thr Val Thr Val Ser Ser Ala Ser Thr Lys Gly Pro
            20                  25                  30

<210> SEQ ID NO 99
<211> LENGTH: 22
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 99

Ala Pro Pro Arg Leu Ile Ser Asp Ser Arg Val Leu Glu Arg Tyr Leu
1               5                   10                  15

Leu Glu Ala Gly Gly Cys
            20

<210> SEQ ID NO 100
<211> LENGTH: 16
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 100

Tyr Leu Leu Glu Ala Lys Glu Ala Glu Asn Ile Thr Thr Gly Gly Cys
1               5                   10                  15

<210> SEQ ID NO 101
<211> LENGTH: 23
<212> TYPE: PRT
<213> ORGANISM: Artificial sequence
<220> FEATURE:
<223> OTHER INFORMATION: Antibody array sequence.

<400> SEQUENCE: 101

Cys Gly Gly Ile Thr Thr Gly Ser Ala Glu His Ser Ser Leu Asn Glu
1               5                   10                  15

Asn Ile Thr Val Pro Asp Thr
            20

<210> SEQ ID NO 102
<211> LENGTH: 27
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (18)..(18)
<223> OTHER INFORMATION: Nle

<400> SEQUENCE: 102

Cys Gly Gly Thr Val Pro Asp Thr Lys Val Asn Phe Tyr Ala Trp Lys
1               5                   10                  15

Arg Xaa Glu Val Gly Gln Gln Ala Val Glu Val
            20                  25

<210> SEQ ID NO 103
<211> LENGTH: 28

```
<212> TYPE: PRT
<213> ORGANISM: Artificial sequence
<220> FEATURE:
<223> OTHER INFORMATION: Antibody array sequence.

<400> SEQUENCE: 103

Cys Gly Gly Gln Ala Val Glu Val Trp Gln Gly Leu Ala Leu Leu Ser
1               5                   10                  15

Glu Ala Val Leu Arg Gly Gln Ala Leu Leu Val Asn
            20                  25

<210> SEQ ID NO 104
<211> LENGTH: 28
<212> TYPE: PRT
<213> ORGANISM: Artificial sequence
<220> FEATURE:
<223> OTHER INFORMATION: Antibody array sequence.

<400> SEQUENCE: 104

Cys Gly Gly Ala Leu Leu Val Asn Ser Ser Gln Pro Trp Glu Pro Leu
1               5                   10                  15

Gln Leu His Val Asp Lys Ala Val Ser Gly Leu Arg
            20                  25

<210> SEQ ID NO 105
<211> LENGTH: 28
<212> TYPE: PRT
<213> ORGANISM: Artificial sequence
<220> FEATURE:
<223> OTHER INFORMATION: Antibody array sequence.

<400> SEQUENCE: 105

Cys Gly Gly Val Ser Gly Leu Arg Ser Leu Thr Thr Leu Leu Arg Ala
1               5                   10                  15

Leu Gly Ala Gln Lys Glu Ala Ile Ser Pro Pro Asp
            20                  25

<210> SEQ ID NO 106
<211> LENGTH: 28
<212> TYPE: PRT
<213> ORGANISM: Artificial sequence
<220> FEATURE:
<223> OTHER INFORMATION: Antibody array sequence.

<400> SEQUENCE: 106

Cys Gly Gly Ile Ser Pro Pro Asp Ala Ala Ser Ala Ala Pro Leu Arg
1               5                   10                  15

Thr Ile Thr Ala Asp Thr Phe Arg Lys Leu Phe Arg
            20                  25

<210> SEQ ID NO 107
<211> LENGTH: 25
<212> TYPE: PRT
<213> ORGANISM: Artificial sequence
<220> FEATURE:
<223> OTHER INFORMATION: Antibody array sequence.

<400> SEQUENCE: 107

Cys Gly Gly Arg Lys Leu Phe Arg Val Tyr Ser Asn Phe Leu Arg Gly
1               5                   10                  15

Lys Leu Lys Leu Tyr Thr Gly Glu Ala
            20                  25

<210> SEQ ID NO 108
```

```
-continued

<211> LENGTH: 15
<212> TYPE: PRT
<213> ORGANISM: Artificial sequence
<220> FEATURE:
<223> OTHER INFORMATION: Antibody array sequence.
<220> FEATURE:
<221> NAME/KEY: MOD_RES
<222> LOCATION: (1)..(1)
<223> OTHER INFORMATION: ACETYLATION

<400> SEQUENCE: 108

Leu Tyr Thr Gly Glu Ala Ser Arg Thr Gly Asp Arg Gly Gly Cys
1               5                   10                  15
```

ANTIBODY ARRAY USED FOR THE ANALYSIS OF THE THREE-DIMENSIONAL STRUCTURE OF PROTEIN THERAPEUTICS AND ITS PRODUCTION

CROSS REFERENCE TO RELATED APPLICATIONS

This application is a U.S. national stage filing under 35 U.S.C. § 371 of PCT International Application No. PCT/US2013/030456, filed Mar. 12, 2013, which claims the benefit of priority to U.S. Application No. 61/610,147, filed Mar. 13, 2012, the disclosures of which is hereby incorporated by reference as if written herein in its entirety.

This application claims the benefit of priority of U.S. provisional Application No. 61/610,147, filed Mar. 13, 2012, the disclosures of which is hereby incorporated by reference as if written herein in its entirety.

BACKGROUND

A protein's three-dimensional structure is closely related to its biological activity. For protein therapeutics (biologics), their three-dimensional structure, to a certain degree, determine their metabolism (PK/PD) and immunogenicity. These are some of the most important parameters besides their biological activities. Because of the importance of protein 3-D structure, several technologies have been used to analyze the 3-D conformation of biologics during their development. The most common technologies include 1) Molecular Sieve or Gel Filtration; 2) Ultracentrifugation; 3) protein fluorescence; 4) CD spectrum; 5) Non-denature gel electrophoresis. However, there are major limitations from these technologies including: 1) low sensitivity: the result can only provide an overall measurement; it can't distinguish differences in a certain region. 2) The analysis is slow, sometimes more than 24 hours are needed for the analysis. 3) Low throughput: only one or a few samples can be analyzed at a time.

Therefore a more sensitive, accurate and fast method is necessary to provide the 3-dimensional structure or conformation of proteins, especially for the development of biologics.

SUMMARY

The invention is based, in part, on the discovery of an antibody array for the analysis of the three-dimensional structure of a protein, as well as methods of using the array to analyze the three-dimensional structure of a protein or to compare the three-dimensional structure of two proteins. Accordingly, in one aspect of the invention, the invention comprises an antibody array that specifically bind to epitopes that cover the surface of a protein and provides a conformational or 3-dimensional structure measurement of said protein. This antibody array provides a method with sensitivity at molecular level; it is systematic to cover the whole sequence of the protein, and providing important information about the 3-D structure of the protein.

In another aspect, the invention comprises a method of determining the conformational or 3-dimensional structure of a protein. The method comprises contacting the protein with an array of antibodies that specifically bind to epitopes that cover the surface of the protein, and measuring the quantity of complex formed between each antibody specifically bound to the protein.

In yet another aspect, the invention comprises a method of comparing the conformational or 3-dimensional structure of a first protein and a second protein. The method comprises contacting each of the first and second proteins with an array of antibodies that specifically bind to epitopes that cover the surface of the first and second proteins, respectively, measuring the quantity of complex formed between each antibody specifically bound to the first and second proteins. The conformational or 3-dimensional structures of the first protein and the second protein are similar if the quantity of complex formed between each antibody specifically bound to the first protein is similar to the quantity of complex formed between each antibody specifically bound to the second protein.

The invention further comprises a kit for assessing the 3-dimensional conformational comparability of a first protein and a second protein to said target therapeutic protein. The kit comprises: a) unique, individual primary antibodies that bind separate peptide fragments of the first protein; b) a compartmentalized substrate, separate compartments of which can be coated with the unique, individual primary antibodies that bind separate peptide fragments of the first protein; c) a reagent solution for blocking any surface of the compartments that remains uncoated by the unique, individual primary antibodies; d) a binding reaction mixture that facilitates binding of the first protein and the second protein to the unique, individual primary antibodies; e) secondary antibodies that comprise, or that can generate, a detectable signal, and which bind the first protein and the second protein; f) a binding reaction mixture that facilitates binding of the secondary antibodies to the first protein and the second protein; g) in the case where the secondary antibodies can generate a detectable signal, reagents for generating the detectable signal; and h) instructions for use of the kit.

DESCRIPTION OF FIGURES

FIG. 8 shows a schematic for PCA ELISA.

FIG. 9 shows d.

DETAILED DESCRIPTION

Figure 1:
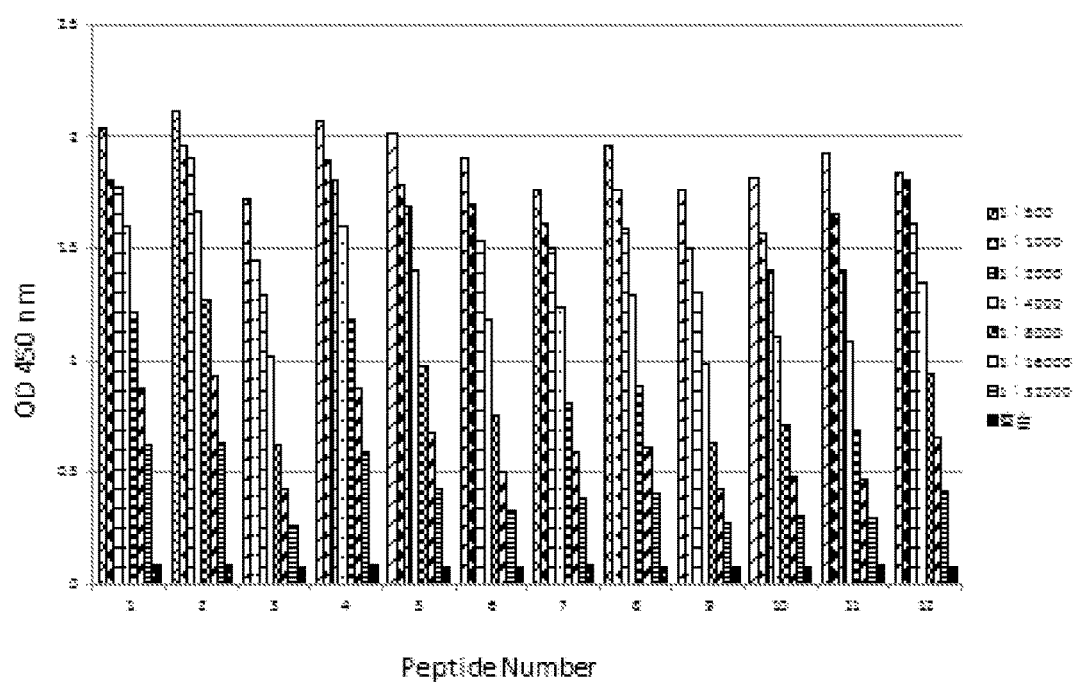
FIG. 1 shows the production of polyclonal antibodies against the peptides of design.

The invention is based on the discovery of an antibody array for the analysis of the three-dimensional structure of a protein, as well as methods of using the array to analyze the three-dimensional structure of a protein or to compare the three-dimensional structure of two proteins. In one aspect of the invention, the invention comprises an antibody array that specifically bind to epitopes that cover the surface of a protein and provides a conformational or 3-dimensional structure measurement of said protein.

In another aspect, the invention comprises a method of determining the conformational or 3-dimensional structure of a protein. The method comprises contacting the protein with an array of antibodies that specifically bind to epitopes that cover the surface of the protein, and measuring the quantity of complex formed between each antibody specifically bound to the protein. The method optionally includes a wash step in between the contacting and measuring steps to remove excess or unbound antibodies.

In one embodiment, the protein, or protein of interest, is an antibody, for example, a monoclonal antibody or a polyclonal antibody. In another embodiment, the protein of interest is not an antibody. In yet another embodiment, the protein of interest is a therapeutic protein including, but not limited to, a therapeutic antibody. The protein of interest could also be an antibody-drug conjugate.

In yet another aspect, the invention comprises a method of comparing the conformational or 3-dimensional structure of a first protein and a second protein. The method comprises contacting each of the first and second proteins with an array of antibodies that specifically bind to epitopes that cover the surface of the first and second proteins, respectively, measuring the quantity of complex formed between each antibody specifically bound to the first and second proteins, and comparing the quantity of each antibody specifically bound to the first and second proteins. The conformational or 3-dimensional structures of the first protein and the second protein are similar if the quantity of complex formed between each antibody bound to the first protein is similar to the quantity of complex formed between each antibody bound to the second protein. The method optionally includes a wash step in between the contacting and measuring steps to remove excess or unbound antibodies.

As above, the first protein and/or the second protein could, but need not be an antibody. If the first protein and/or the second protein are an antibody, they could be a monoclonal antibody or a polyclonal antibody. The protein of interest could also be a therapeutic protein or any protein with three dimensional structure (Higher Order Structure), including, but not limited to, a therapeutic antibody.

In one embodiment, the protein of interest is an antibody. The protein of interest may be a monoclonal antibody or a polyclonal antibody. In one embodiment, the protein of interest is a monoclonal antibody. In another embodiment, the protein of interest is a therapeutic monoclonal antibody. In embodiments of the invention where the protein of interest is an antibody, the capturing antibodies of the array comprise anti-peptide antibodies that are based on the amino acid sequence of the antibody; the reporting antibodies comprise anti-human IgG antibodies, including anti-human IgG1, IgG2, IgG3 and IgG4 antibodies. Human IgG fractions (containing IgG1, IgG2, IgG3 and IgG4) can be used as immunogens to raise antibodies that will have cross-reactivity against the therapeutic protein/antibody. The anti-human IgG antibodies may be monoclonal antibodies or polyclonal antibodies. They can be raised in any known animal, for example, in rabbits. In one embodiment, the antibodies of the array are polyclonal antibodies.

In another embodiment, the protein of interest is not an antibody. The protein of interest could be a therapeutic protein. In embodiments of the invention where the protein of interest is not an antibody, the antibodies of the array comprise antibodies raised against fragments of the protein of interest. The anti-therapeutic protein antibodies may be monoclonal antibodies or polyclonal antibodies and can be raised in any known animal, for example, in rabbits. In one embodiment, the antibodies of the array are polyclonal antibodies. For example, the protein of interest could be Epoetin Alfa, in which case, Epoetin Alfa fragments will be used as immunogens to raise antibodies, e.g., polyclonal antibodies, that will recognize the epitopes on the surface of Epoetin Alfa.

In one embodiment, the antibody array comprises antibodies that specifically bind to overlapping epitopes that cover the surface of the protein, i.e., antibodies that specifically bind to epitopes that comprise overlapping amino acid residues from the protein. In another embodiment, the methods of the invention comprise the step of contacting the protein of interest with an array of antibodies that specifically bind to overlapping epitopes that cover the surface of the protein, i.e., antibodies that specifically bind to epitopes that comprise overlapping amino acid residues from the protein.

In one embodiment, the invention provides a method of comparing the conformational or 3-dimensional structure of a first protein and a second protein, wherein the first protein is, for example, a target therapeutic protein and the second protein is, for example, a putative biosimilar counterpart protein to the target therapeutic protein. The method comprises the steps of:

a) coating separate compartments of a compartmentalized substrate with unique, individual primary antibodies that bind separate peptide fragments of said target therapeutic protein;

b) blocking any surface of said compartments that remains uncoated by said unique, individual primary antibodies;

c) contacting said unique, individual primary antibodies of step b) with said putative biosimilar counterpart and said therapeutic protein in separate binding reaction mixtures;

d) incubating said binding reaction mixtures of step c) for a time and under conditions to permit binding of said putative biosimilar counterpart protein and said therapeutic protein to said unique, individual primary antibodies;

e) removing any unbound putative biosimilar counterpart protein and said therapeutic protein present after incubation in step d);

f) contacting bound putative biosimilar counterpart protein and bound therapeutic protein of step d) and secondary antibodies that comprise, or that can generate, a detectable signal, and which bind said putative biosimilar counterpart protein and said therapeutic protein, in separate binding reaction mixtures;

g) incubating said binding reaction mixtures of step f) for a time and under conditions to permit binding of said secondary antibodies to said putative biosimilar counterpart protein and said therapeutic protein;

h) removing any unbound secondary antibodies present after incubation in step g); and i) detecting, via their detectable signal, secondary antibodies that have bound to said putative biosimilar counterpart protein and said therapeutic protein in step g).

The conformational or 3-dimensional structures of the first protein and the second protein are similar if the quantity of each antibody specifically bound to the first protein is similar to the quantity of each antibody specifically bound to the second protein.

It is to be noted that although the above detailed method has been described with respect to an embodiment in which the first protein is a target therapeutic protein and the second protein is a putative biosimilar counterpart protein to the target therapeutic protein, the process can be used to compare the 3-dimensional structure of any two proteins.

In this embodiment, the unique, individual primary antibodies of step a) can, for example, be raised via immunization of a host with peptide fragments of said first protein or target therapeutic protein. The peptide fragments can be from about 15 amino acids in length to about 50 amino acids in length. In one embodiment, the peptide fragments are about 15, or 20 or 25 or 30 or 35 or 40 or 45 or 50 amino acids in length. In another embodiment, the peptide fragments comprise overlapping amino acids. In one embodiment, the overlapping amino acids comprise from about 1 to about 10 amino acids. In another embodiment, the overlapping amino acids comprise about 1, 2, 3, 4, 5, 6, 7, 8, 9, or about 10 amino acids.

The peptide fragments can be produced by any means known to one of skill in the art. In one embodiment, they are produced by enzymatic digestion of the first protein, e.g., the target therapeutic protein, or by solid phase chemical synthesis.

In general the antibodies of the array or secondary antibodies are detectable, or are optionally bound to a detectable moiety or a moiety that is capable of producing a detectable signal by any means known to one of skill in the art. In one embodiment, the antibodies are biotinylated. The biotinylated antibodies, can, for example, form a complex with streptavidin-horse radish peroxidase that are contacted in a binding reaction mixture and incubated for a time and under conditions to permit the formation of horse radish peroxidase-steptavidin-biotin complexes. The horse radish peroxidase-steptavidin-biotin complexes can be detected by a change in absorbance of a chromogenic substrate oxidizable by horse radish peroxidase upon incubation of said chromogenic oxidizable substrate and the horse radish peroxidase-steptavidin-biotin complexes for a time and under conditions that permit oxidation of said chromogenic oxidizable substrate. In one embodiment, the chromogenic oxidizable substrate is 3,3',5,5'-tetramethylbenzidine (TMB).

The compartmentalized substrate used in the methods or kits (see below) of the invention may be any substrate known to one of skill in the art, including, but not limited to, a 96-well plate. The surface of the compartments that remain uncoated by the individual primary antibodies can be blocked with any solution known to one of skill in the art, including, but not limited to, bovine serum albumin or casein.

The invention further comprises a kit for assessing the 3-dimensional conformational comparability of a first protein and a second protein to said target therapeutic protein. The kit comprises: a) unique, individual primary antibodies that bind separate peptide fragments of the first protein; b) a compartmentalized substrate, separate compartments of which can be coated with the unique, individual primary antibodies that bind separate peptide fragments of the first protein; c) a reagent solution for blocking any surface of the compartments that remains uncoated by the unique, individual primary antibodies; d) a binding reaction mixture that facilitates binding of the first protein and the second protein to the unique, individual primary antibodies; e) secondary antibodies that comprise, or that can generate, a detectable signal, and which bind the first protein and the second protein; f) a binding reaction mixture that facilitates binding of the secondary antibodies to the first protein and the second protein; g) in the case where the secondary antibodies can generate a detectable signal, reagents for generating the detectable signal; and h) instructions for use of the kit.

Protein Conformational Arrays

It is known that the clinical and biological properties of proteins, in general, and biologics, in particular are the results of their basic properties such as amino acid sequence and three-dimensional structure, as well as the production, purification, formulation and storage conditions. One of the major challenges in biologics development is protein immunogenicity. Unwanted immunogenicity could lead to reduced or loss of drug efficacy, altered pharmacokinetics (PK), general immune and hypersensitivity reaction, and neutralization of the natural counterpart in the human body. Multiple studies have demonstrated that protein conformation stability is closely related to its immunogenicity. One recent study indicated that a protein has a threshold of conformational stability to prevent the immunogenicity of foreign proteins. Another strong indication that protein conformation is closely related to its immunogenicity is through the study of protein aggregation. Multiple studies showed that protein aggregation is a major source of immunogenicity.

Recent healthcare legislation in the U.S. has created a pathway for biosimilar approval and commercialization, potentially unleashing a wave of competition to the current class of blockbuster biologics now on the market. However, reconciling the development of these biosimilars with the innovator biologics they are designed to replace has created numerous challenges, a situation which might be summed up as "how similar is similar enough?"

The FDA has outlined the challenges facing the biosimilars approval process and suggested that a "meaningful finger-print-like analysis" would streamline the process and speed the approval process.

The term "biosimilar" is applied to products that have been shown to be similar to the innovator biologic through head to head tests of quality and appropriate comparative studies. If these criteria are met, then the biosimilar can undergo an abbreviated pathway for approval under the Biologics Price Competition and Innovation (BPCI) Act of 2009.

Unlike generic small molecule drugs, biologic drug production is complex, meaning that biosimilars will always be different from the original innovator drug. Even if the biosimilar uses the same gene as the innovator, differences in production, including cloning vector, expression system, fermentation, and purification will generally always result in a biosimilar that is slightly different from the original. The question facing the FDA and biosimilar applicants is, as mentioned above, "how close is close enough?"

The FDA suggests that a "meaningful fingerprint-like" comparison of a large number of product attributes in the innovator and biosimilar products would be very helpful in streamlining the approval process. This appears to be a worthy goal, provided an applicant is able to recognize which product attributes are most critical to compare to a safe and effective biosimilar drug.

In the recently published document for biosimilar development by the Food and Drug Administration (Guidance for Industry, Quality Considerations in Demonstrating Biosimilarity to a Reference Protein Product, FDA, February 2012), the FDA recommends that extensive, robust comparative physicochemical and functional studies should be performed to evaluate whether a proposed biosimilar product and the reference product are highly similar. It states that a meaningful assessment as to whether the proposed biosimilar product is highly similar to the reference product depends on, among other things, the capabilities of available state-of-the-art analytical assays to assess, for example, the molecular weight of the protein, complexity of the protein (higher order structure and post-translational modification), degree of heterogeneity, functional properties, impurity profile, and the degradation profiles denoting stability.

The FDA guidance further states that the three dimensional conformation of a protein is an important factor in its biological function. Proteins generally exhibit complex three-dimensional conformations (tertiary structure nd, in some cases, quaternary structure) due to their large size and the rotational characteristics of protein alpha carbons. The resulting flexibility enables dynamic, but subtle, changes in protein conformation over time, some of which may be absolutely required for functional activity. At the same time, according to the FDA guidance, a protein's three-dimensional conformation can often be difficult to define precisely using current physiochemical analytical technology.

Several analytical techniques and bioassays have been used to probe conformational comparability in biologics. For example, protein intrinsic fluorescence, analytical ultracentrifugation, gel filtration, light scattering and bioassays have all been employed for protein conformational analysis. However, these approaches have their respective limitations as they generally lack the desired sensitivity, coverage and throughput to provide the information about protein 3-dimensional structure. In the case of monoclonal antibody biologics, Bioassays developed based on target-antibody recognition will detect some changes in the CDR (complementarity determining region) regions, but can't measure changes in the rest of the biologics molecule.

Protein Conformational Array drugs could provide a sensitive, systematic and efficient way to measure protein conformational comparability. Protein conformational array antibodies are generally developed from the specific sequence of each protein, for example, a monoclonal antibody drug. About 30 different antibodies can be developed to provide a systematic coverage of the molecule. Studies using marketed monoclonal antibody drugs have indicated (see Examples) that these conformational arrays can provide detailed information about the molecule and detect changes that may not be detected by the aforementioned techniques including bioassays.

Protein Conformational Array ELISA provides a systematic, sensitive and robust comparability testing for testing two proteins, for example, two biologics (therapeutic proteins) at the molecular level. An array of polyclonal antibodies can be designed systematically covering the whole biologics sequence and the assay is in an easy-to-use ELISA format. These Protein Conformational Array ELISAs (PCA ELISA) can provide valuable information on the 3-dimensional structure and heterogeneity of biologics, and can be used at many stages and aspects of biologics development including cell line selection, process development, formulation development and product release testing.

Examples of antibody arrays developed for some known or marketed biologics are provided in the Tables 1-8 below.

TABLE 1

Design of Trastuzumab Antibody Array.

| Peptide Name | Peptide Sequence | AA Number | SEQ ID NO. |
|---|---|---|---|
| Q1* | DIQMTQSPSSLSASVGDRVTITC | 23 | 1 |
| Q2 | CGGRVTITCRASQDVNTAVAWYQQKPG | 27 | 2 |
| Q3 | CGGQQKPGKAPKLLIYSASFLYSGVPSRF | 29 | 3 |
| Q4* | SRFSGSRSGTDFTLTISSLQPEDFATYYC | 29 | 4 |
| Q5 | CGGFATYYSQQHYTTPPTFGQGTK | 24 | 5 |
| Q6 | CGGTKVEIKRTVAAPSVFIFPPSD | 24 | 6 |
| Q7 | CGGIFPPSDEQLKSGTASVVSLLNNFYP | 28 | 7 |
| Q8 | CLLNNFYPREAKVQWKVDNALQ | 22 | 8 |
| Q9 | CGGNALQSGNSQESVTEQDSKDSTYSL | 27 | 9 |
| Q10 | CGGKDSTYSLSSTLTLSKADYEKHKVYASE | 30 | 10 |
| Q11 | CGGKVYASEVTHQGLSSPVTKSFNRGES | 28 | 11 |
| P1 | CGGEVQLVESGGGLVQPGGSLRLS | 24 | 12 |
| P2 | CGGLRLSSAASGFNIKDTYIHWVRQAPG | 28 | 13 |
| P3 | CGGRQAPGKGLEWVARIYPTNGYTRYADS | 29 | 14 |
| P4 | CGGRYADSVKGRFTISADTSKNTAYLQ(nle)N | 29 | 15 |
| P5 | CGGYLQ(nle)NSLRAEDTAVYYCSRWGGDGFY | 29 | 16 |
| P6 | CGGDGFYA(nle)DYWGQGTLVTVSSASTK-GPSV | 30 | 17 |
| P7 | CGGPSVFPLAPSSKSTSGGTAALGSLVK | 28 | 18 |
| P8 | CGGSLVKDYFPEPVTVSWNSGALTSGVHT | 29 | 19 |
| P9 | CGGVHTFPAVLQSSGLYSLSSVVTVPSS | 28 | 20 |
| P10 | CGGVTVPSSSLGTQTYISNVNHKPSNTKV | 29 | 21 |
| P11 | CGGPSNTKVDKKVEPPKSSDKTHTSPPSPA | 30 | 22 |
| P12 | CGGSPPSPAPELLGGPSVFLFPPKPKD | 27 | 23 |
| P13 | CGGSVFLFPPKPKDTL(nle)ISRTPEVT | 25 | 24 |
| P14 | CGGPEVTCVVVDVSHEDPEVKFNWY | 25 | 25 |
| P15 | CGGVKFNWYVDGVEVHNAKTKPREEQYNS | 29 | 26 |
| P16 | CGGQYNSTYRVVSVLTVLHQDWLNGKEYK | 29 | 27 |
| P17 | CGGKEYKSKVSNKALPAPIEKTISKAKGQP | 30 | 28 |
| P18 | CGGKGQPREPQVYTLPPSRDELTKNQVS | 28 | 29 |
| P19 | CGGKNQVSLTSLVKGFYPSDIAVEWESNG | 29 | 30 |
| P20 | CGGWESNGQPENNYKTTPPVLDSDGSF | 27 | 31 |
| P21 | CGGSDGSFFLYSKLTVDKSRWQQGNVFS | 28 | 32 |
| P22 | CGGNVFSSSV(nle)HEALHNHYTQKSLSLSPGK | 30 | 33 |

Where * indicates N-terminal acetylated.

TABLE 2

Design of Rituximab Antibody Array (the Constant Regions are identical to that of Trastuzumab).

| Peptide Name | Peptide Sequence | AA Number | SEQ ID NO. |
|---|---|---|---|
| RiL1* | QIVLSQSPAILSASPGEKVT(nle)TC | 23 | 34 |
| RiL2 | CGGKVT(nle)TSRASSSVSY(nle)HWYQQKPG | 26 | 35 |
| RiL3 | CGGQQKPGSSPKPWIYAPSNLASGVPARF | 29 | 36 |
| RiL4* | ARFSGSGSGTSYSLTISRVEAEDAATYYC | 29 | 37 |
| RiL5 | CGGAATYYSQQWSFNPPTFGAGTK | 24 | 38 |
| RiL6 | CGGAGTKLELKRTVAAPSVFIFPPSD | 26 | 39 |
| RiH1 | CGGQAYLQQSGAELVRPGASVK(nle)S | 24 | 40 |
| RiH2 | CGGVK(nle)SCKASGYTFTSYN(nle)HWVKQTPR | 28 | 41 |
| RiH3 | CGGKQTPRQGLEWIGAIYPGNGDTSYNQK | 29 | 42 |
| RiH4 | CGGSYNQKFKGKATLTVDKSSSTAY(nle)QLS | 29 | 43 |
| RiH5 | CGGY(nle)QLSSLTSEDSAVYFSARVVYYSNS | 29 | 44 |
| RiH6 | CGGYYSNSYWYFDVWGTGTTVTVSGPSV | 28 | 45 |

Where * indicates N-terminal acetylated.

TABLE 3

Design of Bevacizumab Antibody Array (the Constant Regions are identical to that of Trastuzumab).

| Peptide Name | Peptide Sequence | AA Number | SEQ ID NO. |
|---|---|---|---|
| AvL2 | CGGRVTITSSASQDISNYLNWYQQKPG | 27 | 46 |
| AvL3 | CGGQQKPGKAPKVLIYFTSSLHSGVPSRF | 29 | 47 |
| AvL4* | SRFSGSGSGTDFTLTISSLQPEDFATYYC | 29 | 48 |
| AvL5 | CGGFATYYSQQYSTVPWTFGQGTK | 24 | 49 |
| AvH2 | CGGLRLSSAASGYTFTNYG(nle)NWVRQAPG | 28 | 50 |
| AvH3 | CGGRQAPGKGLEWVGWINTYTGEPTYAAD | 29 | 51 |
| AvH4 | CGGTYAADFKRRFTFSLDTSKSTAYLQ(nle)N | 29 | 52 |
| AvH5 | CGGYLQ(nle)NSLRAEDTAVYYSAKYPHYYGSS | 30 | 53 |
| AvH6 | CGGYYGSSHWYFDVWGQGTLVTVSSASTKG | 30 | 54 |

Where * indicates N-terminal acetylated.

TABLE 4

Design of Adalimumab Antibody Array (the Constant Regions are identical to that of Trastuzumab).

| Peptide Name | Peptide Sequence | AA Number | SEQ ID NO. |
|---|---|---|---|
| HuL2 | CGGRVTITSRASQGIRNYLAWYQQ | 24 | 55 |
| HuL3 | CGGQQKPGKAPKLLIYAASTLQSGVPSRFS | 30 | 56 |

TABLE 4-continued

Design of Adalimumab Antibody Array (the Constant Regions are identical to that of Trastuzumab).

| Peptide Name | Peptide Sequence | AA Number | SEQ ID NO. |
|---|---|---|---|
| HuL4* | SRFSGSGSGTDFTLTISSLQPEDVATYYC | 29 | 57 |
| HuL5 | CGGVATYYSQRYNRAPYTFGQGTK | 24 | 58 |
| HuH1* | EVQLVESGGGLVQPGRSLRLSC | 22 | 59 |
| HuH2 | CGGLRLSSAASGFTFDDYA(nle)HWVRQAPG | 28 | 60 |
| HuH3 | CGGRQAPGKGLEWVSAITWNSGHIDYADS | 29 | 61 |
| HuH4 | CGGDYADSVEGRFTISRDNAKNSLYLQ(nle)N | 29 | 62 |
| HuH5 | CGGYLQ(nle)NSLRAEDTAVYYSAKVSYLSTAS | 30 | 63 |
| HuH6 | CGGLSTASSLDYWGQGTLVTVSSASTKGPS | 30 | 64 |

Where * indicates N-terminal acetylated.

TABLE 5

Design of Cetuximab Antibody Array (the Constant Regions are identical to that of Trastuzumab).

| Peptide Name | Peptide Sequence | AA Number | SEQ ID NO. |
|---|---|---|---|
| ErL1* | DILLTQSPVILSVSPGERVSFSC | 23 | 65 |
| ErL2 | CGGRVSFSSRASQSIGTNIHWYQQRTN | 27 | 66 |
| ErL3 | CGGQQRTNGSPRLLIKYASESISGIPSRF | 29 | 67 |
| ErL4 | CGGSRFSGSGSGTDFTLSINSVESEDIADY | 30 | 68 |
| ErL5 | CGGIADYYSQQNNNWPTTFGAGTK | 24 | 69 |
| ErH1* | QVQLKQSGPGLVQPSQSLSITC | 22 | 70 |
| ErH2 | CGGLSITSTVSGFSLTNYGVHWVRQSPG | 28 | 71 |
| ErH3 | CGGRQSPGKGLEWLGVIWSGGNTDYNTP | 28 | 72 |
| ErH4 | CGGDYNTPFTSRLSINKDNSKSQVFFK(nle)N | 29 | 73 |
| ErH5 | CGGFFK(nle)NSLQSNDTAIYYSARALTYY | 27 | 74 |
| ErH6 | CGGALTYYDYEFAYWGQGTLVTVSAASTKG | 30 | 75 |

Where * indicates N-terminal acetylated.

TABLE 6

Design of Alemtuzumab Antibody Array (the Constant Regions are identical to that of Trastuzumab).

| Peptide Name | Peptide Sequence | AA Number | SEQ ID NO. |
|---|---|---|---|
| CaL2 | CGGRVTITSKASQNIDKYLNWYQQKPG | 27 | 76 |
| CaL3 | CGGQQKPGKAPKLLIYNTNNLQTGVPSRF | 29 | 77 |
| CaL4 | CGGSRFSGSGSGTDFTFTISSLQPEDIATY | 30 | 78 |
| CaL5 | CGGIATYYSLQHISRPRTFGQGTK | 24 | 79 |

TABLE 6-continued

Design of Alemtuzumab Antibody Array (the Constant Regions are identical to that of Trastuzumab).

| Peptide Name | Peptide Sequence | AA Number | SEQ ID NO. |
|---|---|---|---|
| CaL6 | CGGQGTKVEIKRTVAAPSVFIFPPSD | 26 | 80 |
| CaH1* | QVQLQESGPGLVRPSQTLSLTC | 22 | 81 |
| CaH2 | CGGLSLTSTVSGFTFTDFY(nle)NWVRQPPG | 28 | 82 |
| CaH3 | CGGRQPPGRGLEWIGFIRDKAKGYTTEYNP | 30 | 83 |
| CaH4 | CGGEYNPSVKGRVT(nle)LVDTSKNQFSLRLS | 29 | 84 |
| CaH5 | CGGSLRLSSVTAADTAVYYSAREGHTAAP | 30 | 85 |
| CaH6 | CGGHTAAPFDYWGQGSLVTVSSASTKGPSV | 30 | 86 |

Where * indicates N-terminal acetylated.

TABLE 7

Design of Palivizumab Antibody Array (the Constant Regions are identical to that of Trastuzumab).

| Peptide Name | Peptide Sequence | AA Number | SEQ ID NO. |
|---|---|---|---|
| SyL1* | DIQ(nle)TQSPSTLSASVGDRVTITC | 23 | 87 |
| SyL2 | CGGRVTITSKSQLSVGY(nle)HWYQQKPG | 26 | 88 |
| SyL3 | CGGQQKPGKAPKLLIYDTSKLASGVPSRF | 29 | 89 |
| SyL4 | CGGSRFSGSGSGTAFTLTISSLQPDDFATY | 30 | 90 |
| SyL5 | CGGFATYYSFQGSGYPFTFGGGTK | 24 | 91 |
| SyL6 | CGGTKLEIKRTVAAPSVFIFPPSD | 24 | 92 |
| SyH1* | QVTLRESGPALVKPTQTLTLTC | 22 | 93 |
| SyH2 | CGGLTLTSTFSGFSLSTSG(nle)SVGWIRQPPG | 30 | 94 |
| SyH3 | CGGRQPPGKALEWLADIWWDDKKDYNPS | 28 | 95 |
| SyH4 | CGGDYNPSLKSRLTISKDTSANQVVLKVT | 29 | 96 |
| SyH5 | CGGVLKVTN(nle)DPADTATYYSARS(nle)IT | 26 | 97 |
| SyH6 | CGGS(nle)ITNWYFDVWGAGTTVTVSSASTKGP | 30 | 98 |

Where * indicates N-terminal acetylated.

TABLE 8

Design of Epoetin Alfa Antibody Array.

| Peptide Name | Peptide Sequence | AA Number | SEQ ID NO. |
|---|---|---|---|
| EP-1* | APPRLISDSRVLERYLLEAGGC | 22 | 99 |
| EP-2* | YLLEAKEAENITTGGC | 16 | 100 |
| EP-3 | CGGITTGSAEHSSLNENITVPDT | 23 | 101 |
| EP-4 | CGGTVPDTKVNFYAWKR(nle)EVGQQAVEV | 27 | 102 |
| EP-5 | CGGQAVEVWQGLALLSEAVLRGQALLVN | 28 | 103 |
| EP-6 | CGGALLVNSSQPWEPLQLHVDKAVSGLR | 28 | 104 |
| EP-7 | CGGVSGLRSLTTLLRALGAQKEAISPPD | 28 | 105 |
| EP-8 | CGGISPPDAASAAPLRTITADTFRKLFR | 28 | 106 |
| EP-9 | CGGRKLFRVYSNFLRGKLKLYTGEA | 25 | 107 |
| EP-10* | LYTGEASRTGDRGGC | 15 | 108 |

Where * indicates N-terminal acetylated.

Also provided herein is a series of Protein Conformation Array ELISA (PCA-ELISA) kits for three-dimensional structural comparability analyses of biologics and biosimilars. These PCA-ELISA kits can provide valuable information on the 3-dimensional structure and heterogeneity of biologics and can be used at many stages of biologics/biosimilars development including cell-line selection, process development, formulation development, and product release testing.

The kit comprises a series of antibodies to peptides spanning the entire length of the amino acid sequence of the biologic (FIG. 8). When used in an ELISA format, with a separate family of polyclonal antibodies in each well of a 96-well plate, one can interrogate the entire surface of the biologics. The series of antibodies can be monoclonal antibodies or polyclonal antibodies. In one embodiment, they are polyclonal antibodies. The antibodies may, in some embodiments target overlapping peptides spanning the entire length of the amino acid sequence of the biologic.

Without being bound to any theory, it is believed that in its native form, few of the epitopes of a protein, e.g., a biologic, will be exposed on the surface of the biologic, but if the higher-order structure of the biologic changes slightly, additional epitopes will be exposed, resulting in a signal increase in the well containing the antibodies to that particular epitope.

Effectively, the kit and methods of the invention provide a "fingerprinting" technique for the native biologic that is also primed to detect very small changes in structure due to the array of antibodies made to all the buried epitopes. The kits and methods provided are highly sensitive to changes in structure or denaturation of the protein and are able to detect as little as 0.1% denaturation of a protein sample (FIG. 9).

In one embodiment, the method comprises an assay that is a robust sandwich-type ELISA and other than a colorimetric plate reader and multichannel pipettes, no specialized lab equipment is needed. Each assay kit comprises, for example, three 96-well plates coated with an array of 15-50 polyclonal antibody families, distributed column-wise across the plates with each polyclonal family represented six times on the plates. In one embodiment, the 96-well plates are coated with an array of 30-31 polyclonal antibody families. In some embodiments, one biosimilar can be compared to innovator in triplicate. In some embodiments, two biosimilars can be compared to innovator in duplicate.

General

As used herein, the terms "therapeutic proteins" and "biologics" are used interchangeably to refer to any protein, for example an antibody or a non-antibody that can be used to prevent, ameliorate the conditions of, or treat any medical condition, disease or disorder.

As used herein, the terms "conformational structure" and "3-dimensional structure" are used interchangeably to refer to the higher-order structure of a protein.

The term "about" in relation to a numerical value x means, for example, x+10%.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1. Antibody Titer Determination

Direct ELISA was used to demonstrate the successful production of polyclonal antibodies against the peptides of design. Different peptides were diluted to 100 µg/ml, 100 µl of the peptide solution was added to the 96-well plate in triplicate, and the plate was coated overnight at 4° C. The next day, the microplate was blocked, and antiserum was diluted to different concentration as shown in FIG. 1 and incubated in the 96-well plate for 1-2 hrs. at room temperature. After washing with PBS-T [Phosphate buffer saline with 0.1% TWEEN® 20 (Tween-20)], secondary antibody, and mouse anti-rabbit IgG-HRP conjugate was added after 1:2,500 dilutions. Incubate at room temperature 1-2 hrs. wash and add TMB substrate to start HRP reaction. After 20 min, the reaction was stopped with 1 M sulfuric acid, and the absorbance was measured at 450 nm.

Example 2. Antibody Specificity

Figure 2:
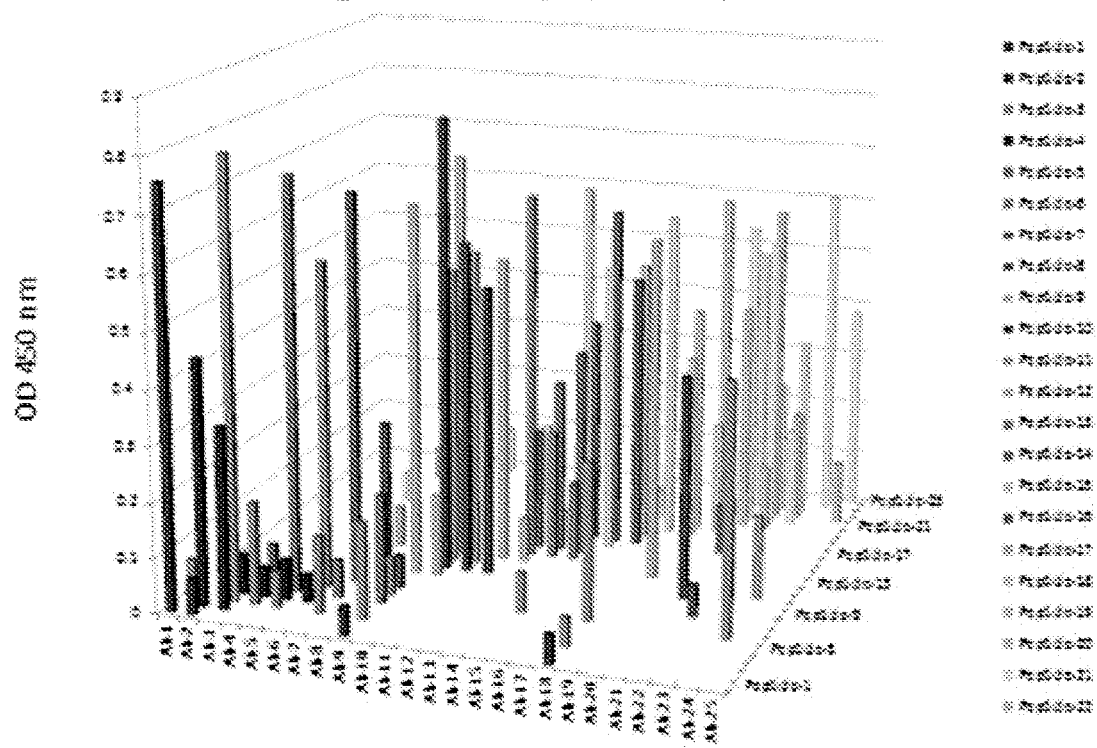
FIG. 2 shows the specificity testing of the antibodies.

One of the major application of the antibody array technology is the capability to detect and quantify regional conformational changes. To carry out this function, antibody specificity is important. In the following specificity testing, similar to the titer testing, different peptides were dissolved into PBS solution and coated onto 96-well plate. In this experiment, every peptide was tested against all the antibodies, and the absorbance of the testing was shown in FIG. 2. As demonstrated, good specificities were achieved with this specific peptide design and antibody production.

Example 3. Conformational Array ELISA from Variable Region

Figure 3:
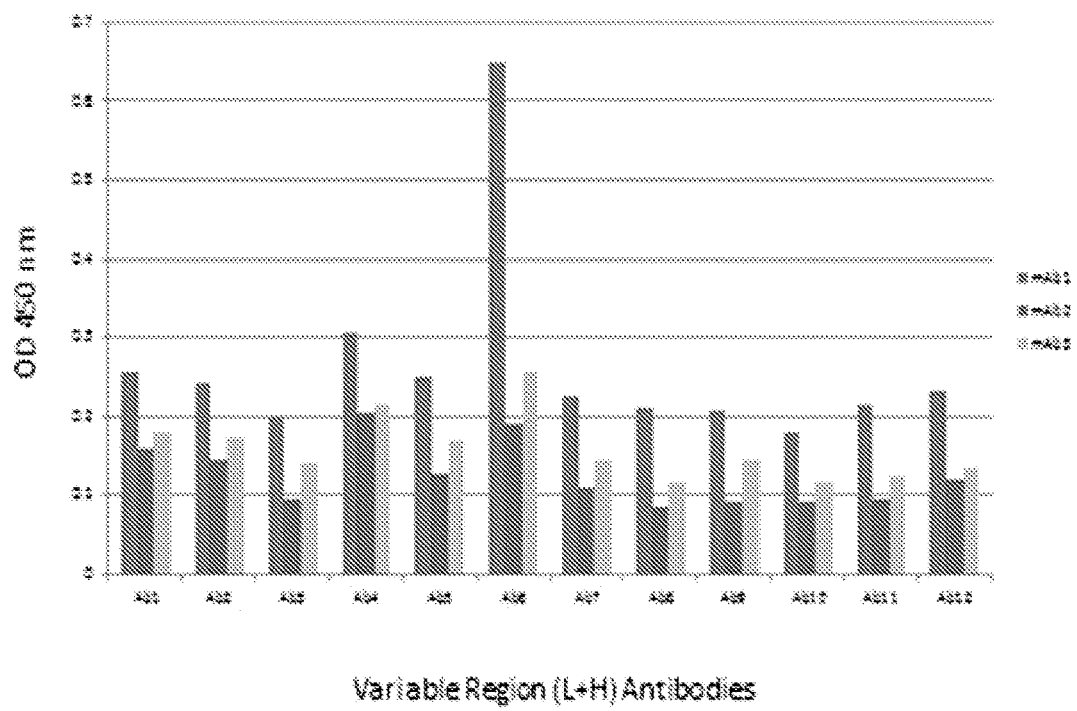
FIG. 3 shows the analysis of conformational changes of three monoclonal antibodies in their variable regions.

One application of the antibody array technology is the analysis of conformational changes, i.e., changes to higher-order structure of novel monoclonal antibodies. As seen in FIG. 3, testing results showed that one set of antibodies composed of the InnoBridge Conformational Array can detect changes to three different novel monoclonal antibodies in its variable region, indicating that this technology can be applied to novel monoclonal antibody discovery and development.

Example 4. Conformational Array ELISA from Constant Region

Similar to experiments in Example 3, testing results showed (see FIG. 4) that one set of antibodies composed of the InnoBridge Conformational Array can detect changes to three different novel antibodies in its constant region, indicating that this technology can be applied to novel monoclonal antibody discovery and development.

Figure 4:
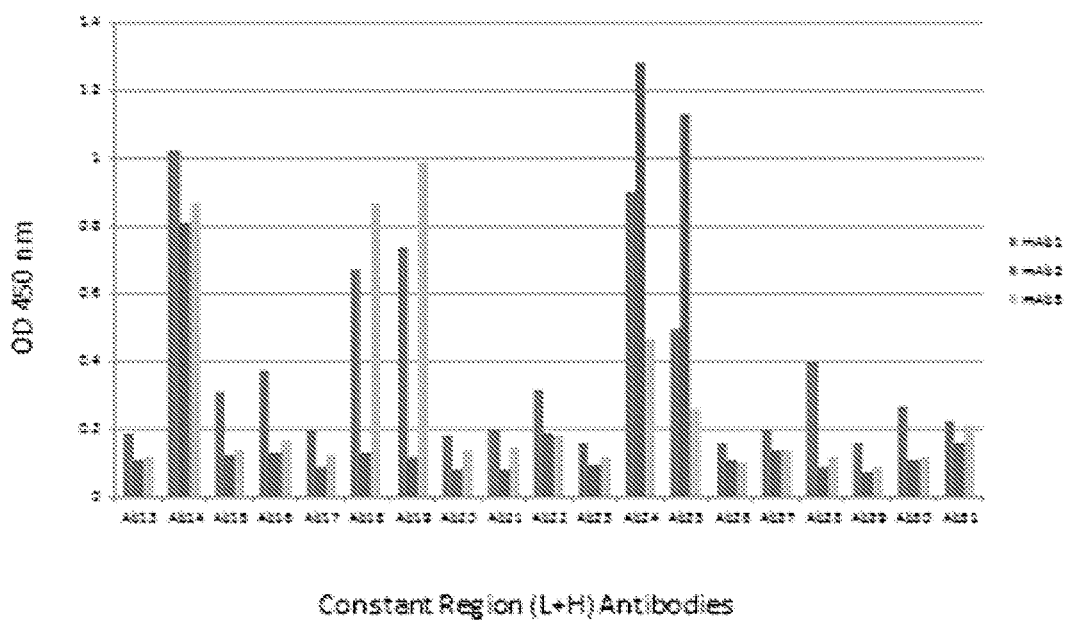
FIG. 4 shows the analysis of conformational changes of three monoclonal antibodies in their constant regions.

FIG. 4 shows three candidate monoclonal antibody drugs that all failed in clinical trials. Two of these candidates showed significant additional epitope exposure to Ab17 and Ab18 (near the hinge region), while the third showed significant epitope exposure to Ab23 and Ab24 (near the glycosylation site). Whether this additional epitope exposure actually caused the clinical trial failure is not yet understood.

Example 5. Variable Region Profiles of Seven Marketed Monoclonal Antibodies

Figure 5:
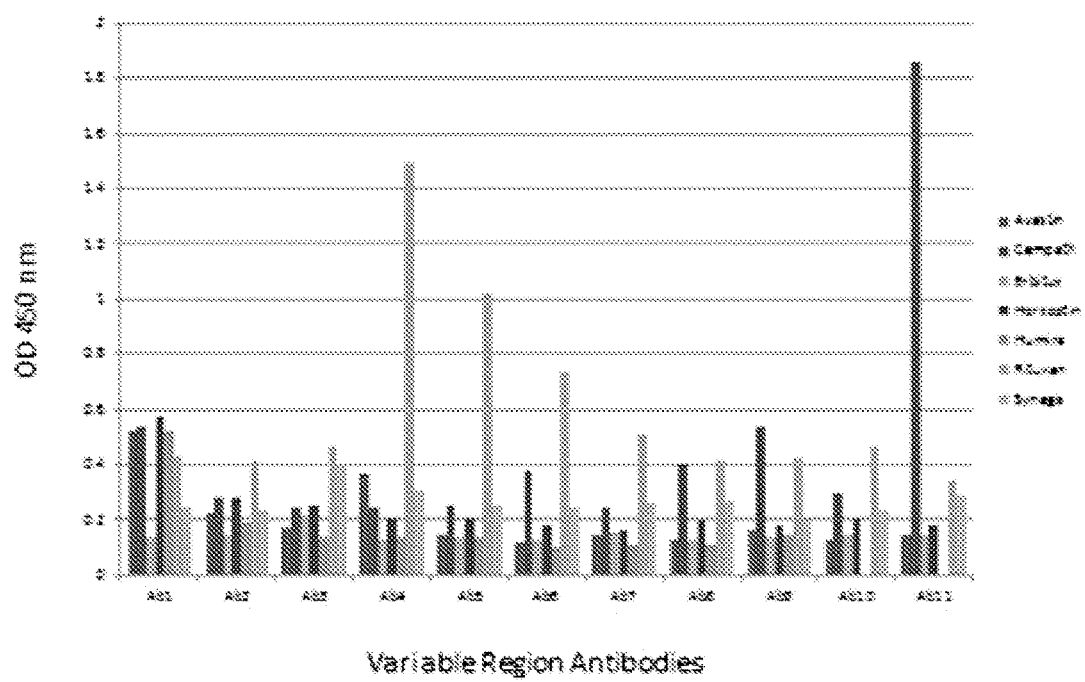
FIG. 5 shows the variable region profiles of seven marketed monoclonal antibodies.

Another application of this antibody array technology is the analysis of higher-order structure or conformational structure comparability between innovator and biosimilar molecules. As seen in FIG. 5, testing results showed that different sets of antibodies corresponding to the seven biosimilar conformational array ELISA can detect changes to its respective innovator monoclonal antibodies in their variable region and each set of antibodies specific to one biosimilar monoclonal antibody generates a unique and stable signal in the ELISA assay, indicating that this technology can be applied to biosimilar monoclonal antibody discovery and development.

Example 6. Constant Region Profiles of Seven Marketed Monoclonal Antibodies

Figure 6:
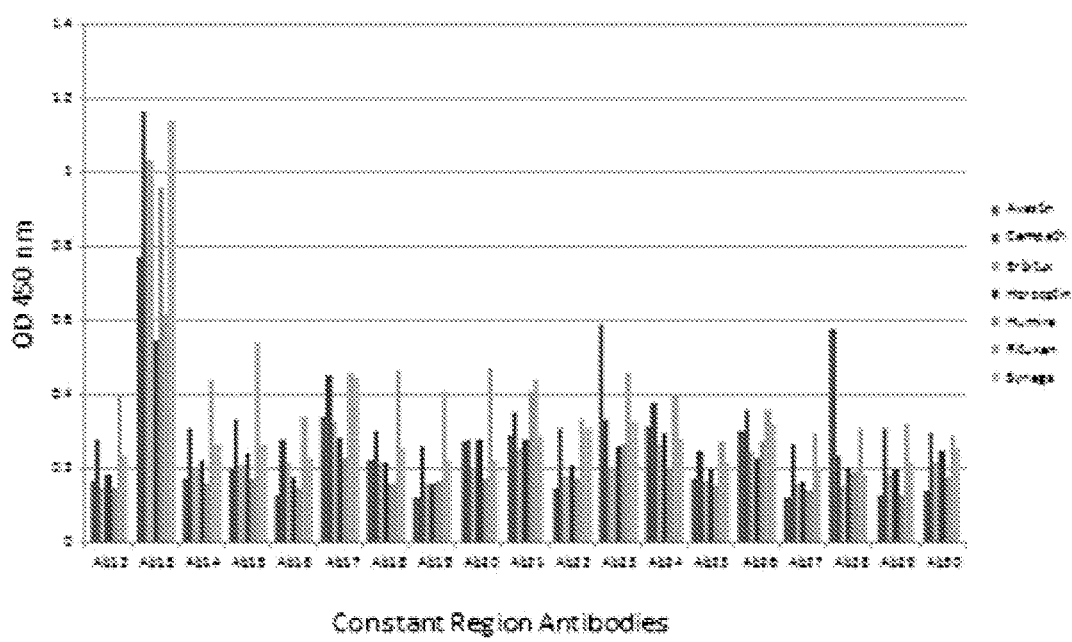
FIG. 6 shows the constant region profiles of seven marketed monoclonal antibodies.

Similar to experiments in Example 5, testing results, as seen in FIG. 6, showed that different sets of antibodies corresponding to the seven biosimilar conformational array ELISA can detect changes to its respective innovator monoclonal antibodies in their constant region, indicating that this technology can be applied to biosimilar monoclonal antibody discovery and development.

FIG. 6 shows the conformational array ELISA result of seven commercially successful monoclonal antibody drugs, with only the Fc (constant region) results depicted. The results are fairly similar across all seven biologics, as would be expected since this region is common among all antibodies in this class.

Example 7. Conformational Array ELISA

Figure 7:
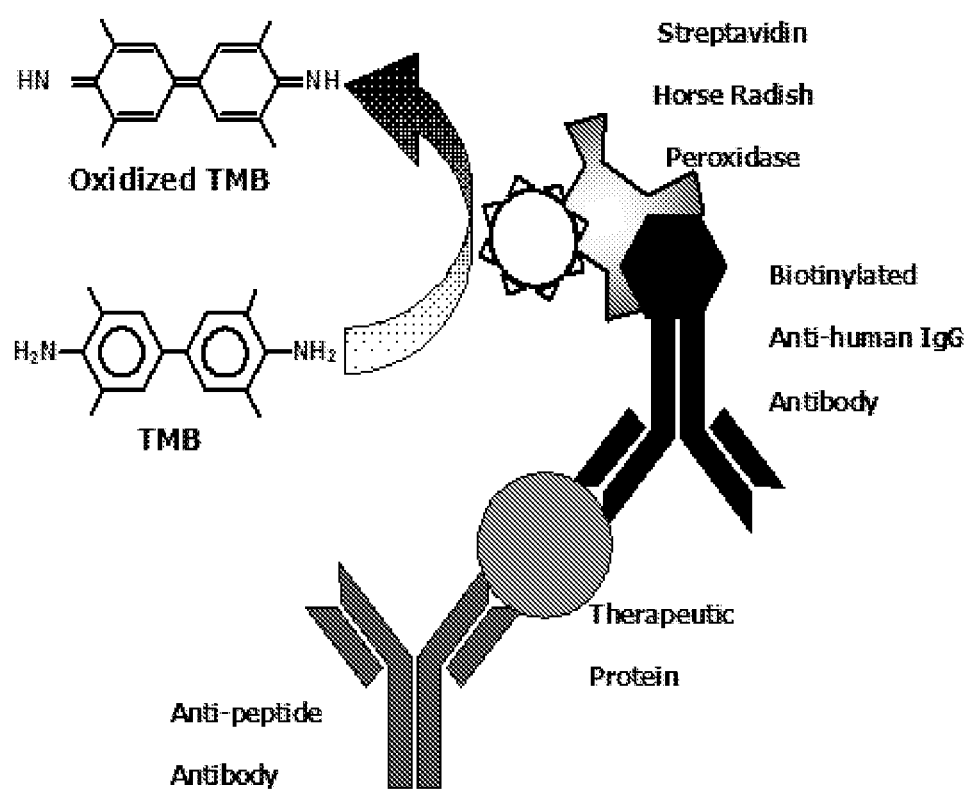
FIG. 7 shows a schematic for an example of a conformational array sandwich ELISA.

FIG. 7 shows a schematic for a conformational array of ELISA of the invention. The protein of interest, for example a therapeutic protein is immobilized on a substrate by capturing antibodies (anti-peptide antibody in FIG. 7). The capturing antibodies are produced using peptides as immunogens, the sequence of the peptides are from the therapeutic protein of interest. Secondary antibodies which are detectable, or attached to a moiety that can produce a detectable signal (e.g., the biotinylated antibody of FIG. 7) are added to the antibody-therapeutic protein complex.

In the embodiment of the invention where the therapeutic protein is an antibody, for example monoclonal antibodies like Herceptin, then the secondary antibodies are anti-human IgG antibodies. Human IgG fractions (containing IgG1, IgG2, IgG3 and IgG4) were used as immunogens to raise polyclonal antibodies against the therapeutic protein in rabbits. These antibodies will recognize the anti-peptide-monoclonal antibody complex formed. In the embodiment of the invention where the therapeutic protein is not an antibody, for example, Epoetin Alfa, then Epoetin Alfa fragments will be used as immunogens to raise polyclonal antibodies in rabbit, and these antibodies will recognize the anti-peptide-epoetin alfa complex.

Since the anti-therapeutic protein antibody is biotinylated, it will form a complex with streptavidin-HRP which in turn will catalyze a color change when the HRP substrate, TMB is added. The signal of the color change will indicate how many therapeutic protein complexes are in the system.

What is claimed is:

1. A method of determining the conformational or 3-dimensional structure of a protein comprising:
   (a) contacting said protein with an array of antibodies that specifically bind to epitopes that cover the surface of said protein; and
   (b) measuring the quantity of complex formed between each antibody specifically bound to said protein;
   wherein the quantity of complex formed between each of the antibodies of the array and the protein is used to determine the conformational or 3-dimensional structure of the protein.

2. A method of comparing the conformational or 3-dimensional structure of a first protein and a second protein comprising: contacting each of said first and second proteins with an array of antibodies that specifically bind to epitopes that cover the surface of said first and second proteins, respectively; measuring the quantity of complex formed between each antibody specifically bound to said first and second proteins; and comparing the quantity of complex formed between each antibody specifically bound to said first and second proteins, wherein the conformational or 3-dimensional structures of said first protein and said second protein are similar if the quantity of complex formed between each antibody specifically bound to said first protein is similar to the quantity of complex formed between each antibody specifically bound to said second protein.

3. The method of claim 1, wherein said epitopes that cover the surface of said protein comprise overlapping amino acid residues from said protein.

4. The method of claim 2, wherein the first protein is a target therapeutic protein and the second protein is a putative biosimilar counterpart protein to said target therapeutic protein, comprising the following steps prior to the comparing step:
   a. coating separate compartments of a compartmentalized substrate with unique, individual primary antibodies that bind separate peptide fragments of said target therapeutic protein;
   b. blocking any surface of said compartments that remains uncoated by said unique, individual primary antibodies;
   c. contacting said unique, individual primary antibodies of step b) with said putative biosimilar counterpart and said therapeutic protein in separate binding reaction mixtures;
   d. incubating said binding reaction mixtures of step c) for a time and under conditions to permit binding of said putative biosimilar counterpart protein and said therapeutic protein to said unique, individual primary antibodies;
   e. removing any unbound putative biosimilar counterpart protein and said therapeutic protein present after incubation in step d);
   f. contacting bound putative biosimilar counterpart protein and bound therapeutic protein of step d) and secondary antibodies that comprise, or that can generate, a detectable signal, and which bind said putative biosimilar counterpart protein and said therapeutic protein, in separate binding reaction mixtures;
   g. incubating said binding reaction mixtures of step f) for a time and under conditions to permit binding of said secondary antibodies to said putative biosimilar counterpart protein and said therapeutic protein;
   h. removing any unbound secondary antibodies present after incubation in step g); and
   i. detecting, via their detectable signal, secondary antibodies that have bound to said putative biosimilar counterpart protein and said therapeutic protein in step g).

5. The method of claim 4, wherein said unique, individual primary antibodies of step a) are raised via immunization of a host with peptide fragments of said target therapeutic protein.

6. The method of claim 5, wherein said peptide fragments are about 15 to about 50 amino acids in length.

7. The method of claim 5, wherein said peptide fragments comprise overlapping amino acids.

8. The method of claim 7, wherein said overlapping amino acids comprise from about 1 to about 10 amino acids.

9. The method of claim 5, wherein said peptide fragments are produced by enzymatic digestion of said target therapeutic protein, or by solid phase chemical synthesis.

10. The method of claim 4, wherein said target therapeutic protein is a monoclonal antibody or a non-antibody, pharmaceutically active protein.

11. The method of claim 4, wherein said target therapeutic protein is a monoclonal antibody, and said secondary antibodies of step f) are polyclonal antibodies raised against human IgG, including IgG1, IgG2, IgG3, and IgG4, purified from human serum.

12. The method of claim 4, wherein said target therapeutic protein is a non-antibody, pharmaceutically active protein, and said secondary antibodies of step f) are polyclonal antibodies raised against said non-antibody, pharmaceutically active protein.

13. The method of claim 11, wherein said secondary antibodies are biotinylated.

14. The method of claim 13, wherein said biotinylated secondary antibodies and a streptavidin-horse radish peroxidase conjugate are contacted in a binding reaction mixture and incubated for a time and under conditions to permit the formation of horse radish peroxidase-streptavidin-biotin complexes.

15. The method of claim 14, wherein said horse radish peroxidase-streptavidin-biotin complexes are detected by a change in absorbance of a chromogenic substrate oxidizable by horse radish peroxidase upon incubation of said chromogenic oxidizable substrate and said horse radish peroxidase-streptavidin-biotin complexes for a time and under conditions that permit oxidation of said chromogenic oxidizable substrate.

16. The method of claim 15, wherein said chromogenic oxidizable substrate is 3,3',5,5'-tetramethylbenzidine (TMB).

17. The method of claim 4, wherein said target therapeutic protein and said putative biosimilar counterpart protein are each an antibody-drug conjugate.

* * * * *